United States Patent [19]

Schallner et al.

[11] Patent Number: 4,812,165
[45] Date of Patent: Mar. 14, 1989

[54] SUBSTITUTED 1-ARYLPYRAZOLES, COMPOSITIONS AND USE

[75] Inventors: Otto Schallner, Monheim; Reinhold Gehring; Jörg Stetter, both of Wuppertal; Hans-Joachim Santel, Leverkusen; Robert R. Schmidt; Klaus Lürssen, both of Bergisch-Gladbach; Harry Strang, Düsseldorf, all of Fed. Rep. of Germany

[73] Assignee: Bayer Aktiengesellschaft, Leverkusen, Fed. Rep. of Germany

[21] Appl. No.: 164,673

[22] Filed: Mar. 7, 1988

[30] Foreign Application Priority Data

Mar. 10, 1987 [DE] Fed. Rep. of Germany ....... 3707551

[51] Int. Cl.$^4$ .................... A01N 43/40; A01N 43/56; C07D 231/16; C07D 401/04
[52] U.S. Cl. ........................................... 71/92; 71/72; 71/74; 546/279; 548/375; 548/376
[58] Field of Search ................ 548/375, 376; 546/279; 71/92, 72, 74

[56] References Cited

U.S. PATENT DOCUMENTS 4,459,150 7/1984 Hatton et al. ........................... 71/92

OTHER PUBLICATIONS

Chemical Abstract Band 107, Nov. 23, 1987, No. 198,317c.
Chemical Abstract, Band 107, Dec. 1986, No. 217,623t.

Primary Examiner—Robert W. Ramsuer
Attorney, Agent, or Firm—Sprung Horn Kramer & Woods

[57] ABSTRACT

Herbicidal and plant growth-regulating compounds of the formula

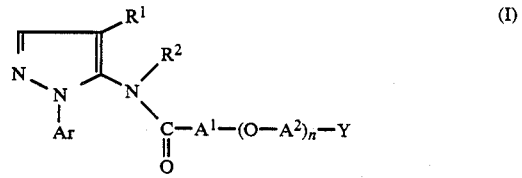

in which
$R^1$ represents hydrogen or nitro,
$R^2$ represents hydrogen, alkyl or a radical

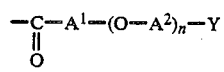

$A^1$ and $A^2$ independently of each other each represent a divalent alkylene radical,
Y represents halogen, hydroxyl, optionally substituted alkoxy, optionally substituted aryloxy or a radical

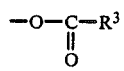

$R^3$ represents hydrogen, alkyl, alkoxy, amino, alkylamino, dialkylamino or in each case optionally substituted aryl, aryloxy or arylamino,
Ar represents in each case optionally substituted phenyl or pyridyl and
n represents a number 1, 2, 3 or 4.

12 Claims, No Drawings

SUBSTITUTED 1-ARYLPYRAZOLES, COMPOSITIONS AND USE

The invention relates to new substituted 1-arylpyrazoles, several processes for their preparation and also their use as herbicides and plant growth regulators.

It is already known that certain 1-arylpyrazoles such as, for example, 4-cyano-5-propionamido-1-(2,4,6-trichlorophenylpyrazole) possess herbicidal properties (cf. for example DE-OS (German Published Specification) No. 3,226,513).

The herbicidal activity of these previously known compounds towards problem weeds is however, like their compatability towards important useful plants, not always completely satisfactory in all fields of application.

New substituted 1-arylpyrazoles of the general formula (I), $$\text{(I)}$$

in which
$R^1$ represents hydrogen or nitro,
$R^2$ represents hydrogen, alkyl or a radical $$-\underset{\underset{O}{\|}}{C}-A^1-(O-A^2)_n-Y,$$

$A^1$ and $A^2$ independently of each other each represent a divalent alkylene radical, Y represents halogen, hydroxyl, optionally substituted alkoxy, optionally substituted aryloxy or a radical $$-O-\underset{\underset{O}{\|}}{C}-R^3,$$

$R^3$ represents hydrogen, alkyl, alkoxy, amino, alkylamino, dialkylamino or in each case optionally substituted aryl, aryloxy or arylamino, Ar represents in each case optionally substituted phenyl or pyridyl and n represents a number 1, 2, 3 or 4,
have been found.

Furthermore, it has been found that the new substituted 1-arylpyrazoles of the general formula (I), $$\text{(I)}$$

in which
$R^1$ represents hydrogen or nitro,
$R^2$ represents hydrogen, alkyl or a radical $$-\underset{\underset{O}{\|}}{C}-A^1-(O-A^2)_n-Y,$$

$A^1$ and $A^2$ independently of each other each represent a divalent alkylene radical, Y represents halogen, hydroxyl, optionally substituted alkoxy, optionally substituted aryloxy or a radical $$-O-\underset{\underset{O}{\|}}{C}-R^3,$$

$R^3$ represents hydrogen, alkyl, alkoxy, amino, alkylamino, dialkylamino or in each case optionally substituted aryl, aryloxy or arylamino, Ar represents in each case optionally substituted phenyl or pyridyl and n represents a number 1, 2, 3 or 4,
are obtained by one of the processes described below:

(a) substituted 1-arylpyrazoles of the formula (Ia), $$\text{(Ia)}$$

in which $R^1$, $A^1$, $A^2$, Y, Ar and n have the meanings given above and $R^{2-1}$ represents hydrogen or a radical $$-\underset{\underset{O}{\|}}{C}-A^2-(O-A^1)_n-Y,$$

are obtained when 5-amino-1-aryl-pyrazoles of the formula (II), $$\text{(II)}$$

in which $R^1$ and Ar have the meanings given above, are reacted with acylating agents of the formula (III), $$Hal^1-\underset{\underset{O}{\|}}{C}-A^1-(O-A^2)_n-Y \quad \text{(III)}$$

in which
$Hal^1$ represents halogen and
$A^1$, $A^2$, Y and n have the meanings given above,
optionally in the presence of a diluent, optionally in the presence of an acid binding agent and optionally in the presence of a catalyst;

(b) substituted 1-arylpyrazoles of the formula (Ib),

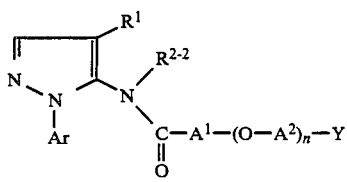

in which
R²⁻² represents alkyl and
R¹, A¹, A², Y, Ar and n have the meanings given above, are obtained when substituted 1-arylpyrazoles of the formula (Ic),

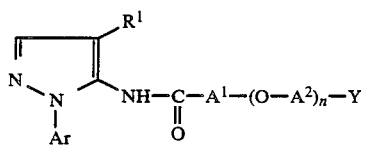

in which R¹, A¹, A², Y, Ar and n have the meanings given above, are reacted with alkylating agents of the formula (IV), $$R^{2-2}-E \quad (IV)$$

in which
R²⁻² represents alkyl and
E represents an electron-withdrawing leaving group, optionally in the presence of a diluent and optionally in the presence of an acid binding agent and also optionally in the presence of a catalyst;

(c) 4-nitro-1-aryl-pyrazoles of the formula (Id),

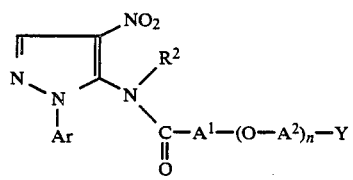

in which R², A¹, A², Y, Ar and n have the meanings given above, are obtained when substituted 1-arylpyrazoles of the formula (Ie),

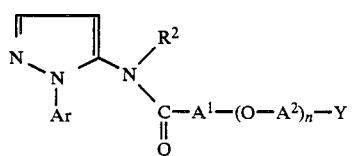

in which R², A¹, A², Y, Ar and n have the meanings given above, are reacted with a nitrating agent optionally in the presence of a diluent and optionally in the presence of a catalyst or reaction auxiliary;

(d) substituted 1-arylpyrazoles of the formula (If),

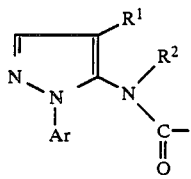

in which R¹, R², R³, A¹, A², Ar and n have the meanings given above, are obtained when 1-arylpyrazoles of the formula (Ig),

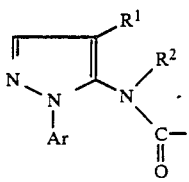

in which R¹, R², A¹, A², Ar and n have the meanings given above, are reacted with acylating agents of the formula (VI),

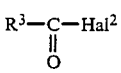

in which
Hal² represents halogen and
R³ has the meaning given above,
optionally in the presence of a diluent, optionally in the presence of an acid binding agent and optionally in the presence of an acylation catalyst.

Finally, it has been found that the new substituted 1-arylpyrazoles of the general formula (I) possess herbicidal, in particular also selective herbicidal, and plant growth-regulating properties.

Surprisingly, the substituted 1-arylpyrazoles of the general formula (I) according to the invention, besides a considerably improved general herbicidal activity against problem weeds which are difficult to combat, exhibit a clearly improved compatibility with important crop plants compared to the 1-arylpyrazoles which are known from the prior art, such as, for example, 4-cyano-5-propionamido-1-(2,4,6-trichlorophenyl)-pyrazole, which are related compounds chemically and in respect of their action, and, completely unexpectedly, additionally also exhibit plant growth-regulating properties.

Formula (I) provides a general definition of the substituted 1-arylpyrazoles according to the invention. Preferred compounds of the formula (I) are those in which
R¹ represents hydrogen or nitro,
R² represents hydrogen, straight-chain or branched alkyl having 1 to 12 carbon atoms or a

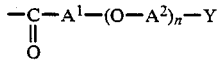

radical, in which
A¹ and A², independently of one another, in each case represent an in each case straight-chain or branched divalent alkylene radical having 1 to 6 carbon atoms, Y represents halogen, hydroxyl, straight-chain or branched alkoxy having 1 to 6 carbon atoms which is optionally monosubstituted or polysubstituted by halogen, cyano or nitro, the substituents being identical or different, or optionally monosubstituted or polysubstituted phenyloxy, these substituents being identical or different and suitable substituents being: halogen, cyano, nitro, in each case straight-chain or branched alkyl, alkoxy, alkylthio, halogenoalkyl, halogenoalkoxy, halogenoalkylthio or alkoxycarbonyl in each case having 1 to 4 carbon atoms and, if appropriate, 1 to 9 identical or different halogen atoms; in addition represents a

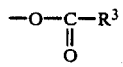

radical, where

R³ represents hydrogen, amino, in each case straight-chain or branched alkyl, alkoxy, alkylamino or dialkylamino in each case having 1 to 6 carbon atoms in the individual alkyl parts, or in each case optionally monosubstituted or polysubstituted phenyl, phenoxy or phenylamino, the substituents being identical or different and suitable substituents being in each case: halogen, cyano, nitro, in each case straight-chain or branched alkyl, alkoxy, alkylthio, halogenoalkyl, halogenoalkoxy, halogenoalkylthio or alkoxycarbonyl in each case having 1 to 4 carbon atoms, and, if appropriate, 1 to 9 identical or different halogen atoms, Ar represents in each case optionally monosubstituted or polysubstituted phenyl, 2-pyridyl, 3-pyridyl or 4-pyridyl, the substituents being identical or different and suitable substituents being in each case: halogen, cyano, nitro, in each case straight-chain or branched alkyl, alkoxy or alkoxycarbonyl, in each case having 1 to 4 carbon atoms in the alkyl parts, in each case straight-chain or branched halogenoalkyl or halogenoalkoxy in each case having 1 to 4 carbon atoms and 1 to 9 identical or different halogen atoms, or a —S(O)$_m$—R⁴ radical where R⁴ represents amino, in each case straight-chain or branched alkyl, alkylamino, dialkylamino or halogenoalkyl, in each case having 1 to 4 carbon atoms in the individual alkyl parts and, in the case of halogenoalkyl, having 1 to 9 identical or different halogen atoms, m represents a number 0, 1 or 2, and n represents a number 1, 2, 3 or 4.

Particularly preferred substituted 1-arylpyrazoles of the general formula (I) are those in which R¹ represents hydrogen or nitro, R² represents hydrogen, straight-chain or branched alkyl having 1 to 8 carbon atoms or a

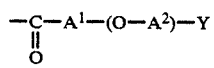

radical,

A¹ and A², independently of one another, in each case represent an in each case straight-chain or branched divalent alkylene radical having 1 to 4 carbon atoms, Y represents fluorine, chlorine, bromine, iodine, hydroxyl, straight-chain or branched alkoxy having 1 to 4 carbon atoms, or optionally monosubstituted, disubstituted or trisubstituted phenyloxy, the substituents being identical or different and suitable substituents being: fluorine, chlorine, bromine, cyano, nitro, methyl, ethyl, n- or i-propyl, n-, i-, s- or t-butyl, methoxy, ethoxy, methylthio, trifluoromethyl, trifluoromethoxy, trifluoromethylthio, methoxycarbonyl or ethoxycarbonyl; in addition represents a

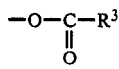

radical,

R³ represents hydrogen, amino, in each case straight-chain or branched alkyl, alkoxy, alkylamino or dialkylamino in each case having 1 to 4 carbon atoms in the individual alkyl parts, or in each case optionally monosubstituted, disubstituted or trisubstituted phenyl, phenoxy or phenylamino, the substituents being identical or different and suitable substituents being in each case: fluorine, chlorine, bromine, cyano, nitro, methyl, ethyl, n- or i-propyl, n-, i-, s- or t-butyl, methoxy, ethoxy, methylthio, trifluoromethyl, trifluoromethoxy, trifluoromethylthio, methoxycarbonyl or ethoxycarbonyl, Ar represents optionally monosubstituted to pentasubstituted phenyl, the substituents being identical or different, or in each case optionally monosubstituted to tetrasubstituted 2-pyridyl, 3-pyridyl or 4-pyridyl, the substituents being identical or different and suitable substituents being in each case: cyano, nitro, fluorine, chlorine, bromine, iodine, methyl, ethyl, n- or i-propyl, n-, i-, s- or t-butyl, methoxy, ethoxy, methoxycarbonyl, ethoxycarbonyl, trifluoromethyl, trichloromethyl, dichlorofluoromethyl, difluorochloromethyl, chloromethyl, dichloromethyl, difluoromethyl, pentafluoroethyl, tetrafluoroethyl, trifluorochloroethyl, trifluoroethyl, difluorodichloroethyl, trifluorodichloroethyl, pentachloroethyl, trifluoromethoxy, trichloromethoxy, dichlorofluoromethoxy, difluorochloromethoxy, chloromethoxy, dichloromethoxy, difluoromethoxy, pentafluoroethoxy, tetrafluoroethoxy, trifluorochloroethoxy, trifluoroethoxy, difluorodichloroethoxy, trifluorodichloroethoxy, pentachloroethoxy or an —S(O)$_m$—R⁴ radical, R⁴ represents amino, methylamino, ethylamino, dimethylamino, diethylamino, fluorodichloromethyl, difluoromethyl, tetrafluoroethyl, trichloroethyl, trifluoromethyl, difluorochloromethyl, methyl or ethyl, m represents a number 0, 1 or 2, and n represents a number 1, 2, 3 or 4.

Very particularly preferred compounds of the formula (I) are those in which

R¹ represents nitro,

R² represents hydrogen, methyl, ethyl, n- or i-propyl, a n-, i-, s- or t-butyl or a

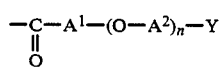

radical,

A¹ and A², independently of one another, in each case represent a bridging group of the formula —CH$_2$—; —CH$_2$—CH$_2$—;

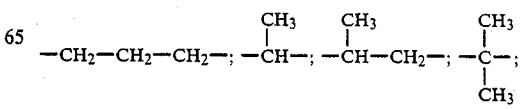

-continued $$-\underset{\underset{CH_3}{|}}{\overset{\overset{CH_3}{|}}{C}}-CH_2-; \quad -\underset{\underset{C_2H_5}{|}}{CH}-; \text{ or } -\underset{\underset{C_2H_5}{|}}{CH}-CH_2-,$$

Y represents fluorine, chlorine, bromine, methoxy, ethoxy, n- or i-propoxy, n- or i-butoxy or hydroxyl, Ar represents optionally monosubstituted to pentasubstituted phenyl, the substituents being identical or different, or optionally monosubstituted to tetrasubstituted 2-pyridyl, the substituents being identical or different and suitable substituents being in each case: cyano, nitro, fluorine, chlorine, bromine, iodine, methyl, ethyl, n- or i-propyl, n-, i-, s- or t-butyl, methoxy, ethoxy, methoxycarbonyl, ethoxycarbonyl, trifluoromethyl, trichloromethyl, dichlorofluoromethyl, difluorochloromethyl, chloromethyl, dichloromethyl, difluoromethyl, pentafluoroethyl, tetrafluoroethyl, trifluorochloroethyl, trifluoroethyl, difluorodichloroethyl, trifluorodichloroethyl, pentachloroethyl, trifluoromethoxy, trichlorometnoxy, dichlorofluoromethoxy, difluorochloromethoxy, chloromethoxy, dichloromethoxy, difluoromethoxy, pentafluoroethoxy, tetrafluoroethoxy, trifluorochloroethoxy, trifluoroethoxy, difluorodichloroethoxy, trifluorodichloroethoxy, pentachloroethoxy or an $-S(O)_m-R^4$ radical, where $R^4$ represents amino, methylamino, ethylamino, dimethylamino, diethylamino, fluorodichloromethyl, difluoromethyl, tetrafluoroethyl, trichloroethyl, trifluoromethyl, difluorochloromethyl, methyl or ethyl, m represents a number 0, 1 or 2 and n represents a number 1 or 2.

In addition to the compounds mentioned in the preparation examples, the following substituted 1-arylpyrazoles of the general formula (I) may be mentioned individually:

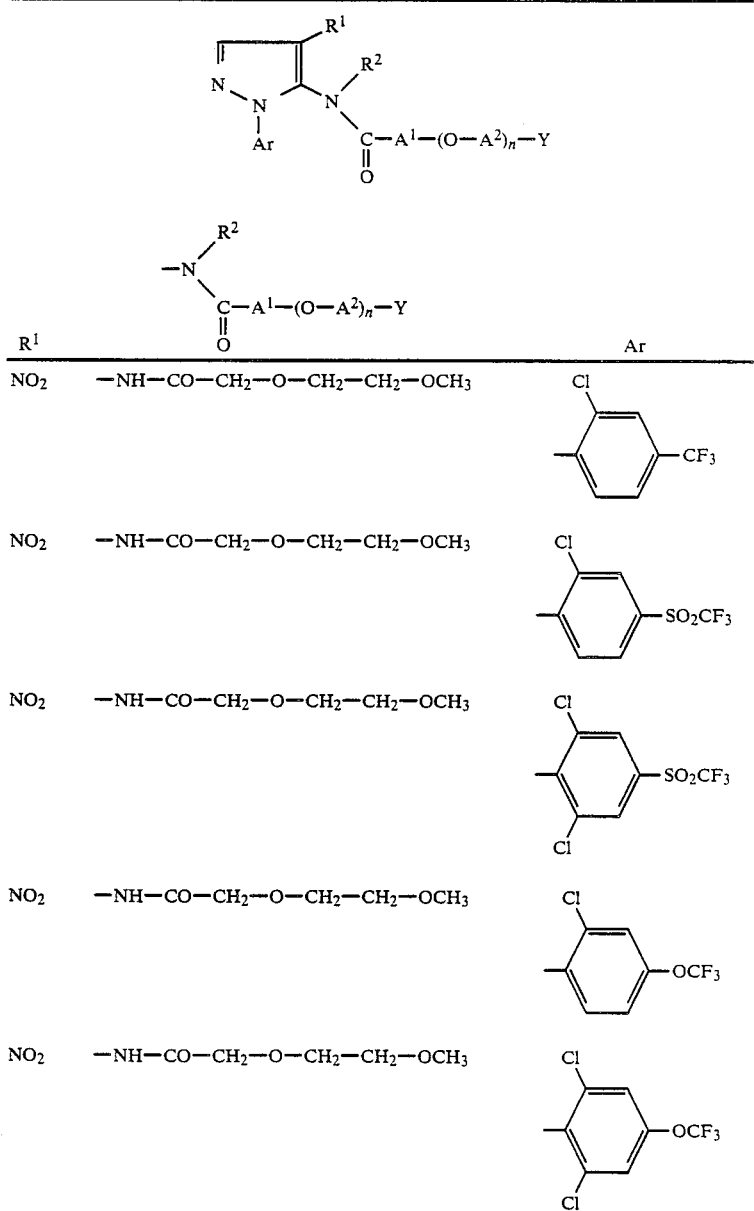

-continued
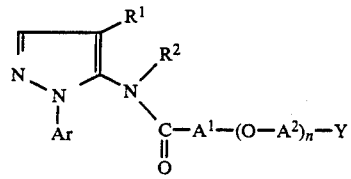
| R¹ | $-N\overset{R^2}{\underset{\underset{O}{C-A^1-(O-A^2)_n-Y}}{}}$ | Ar |
|---|---|---|
| NO₂ | —NH—CO—CH₂—O—CH₂—CH₂—OCH₃ | 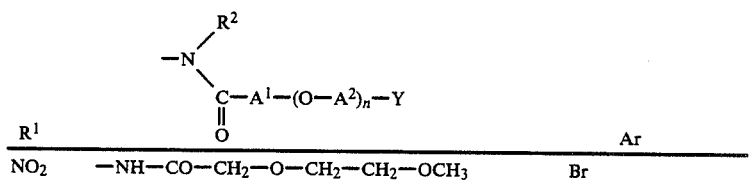 |
| NO₂ | —NH—CO—CH₂—O—CH₂—CH₂—OCH₃ |  |
| NO₂ | —NH—CO—CH₂—O—CH₂—CH₂—OCH₃ | 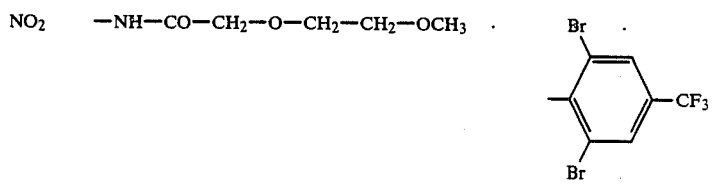 |
| NO₂ | —NH—CO—CH₂—O—CH₂—CH₂—OCH₃ | 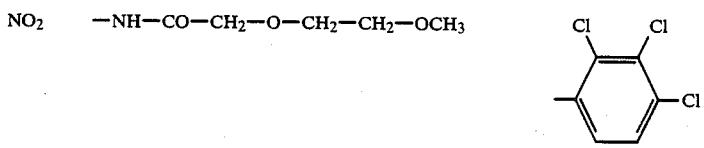 |
| NO₂ | —NH—CO—CH₂—O—CH₂—CH₂—OCH₃ | 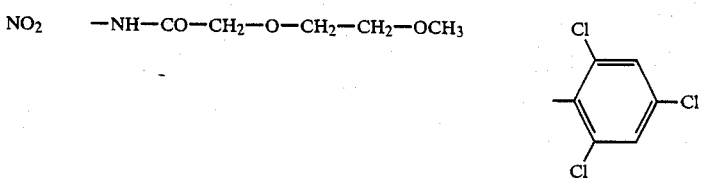 |
| NO₂ | —NH—CO—CH₂—O—CH₂—CH₂—OCH₃ | 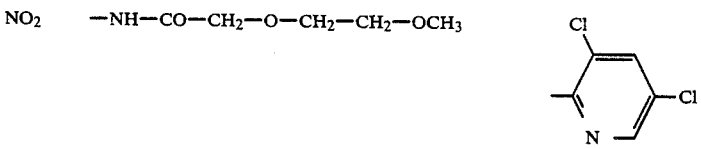 |
| NO₂ | —NH—CO—CH₂—O—CH₂—CH₂—OCH₃ | 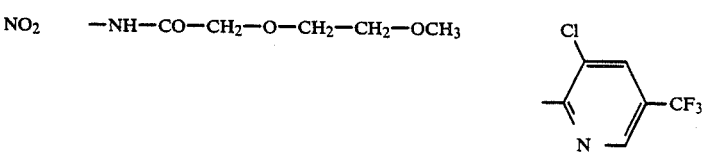 |
| NO₂ | —NH—CO—CH₂—O—CH₂—CH₂—OCH₃ | 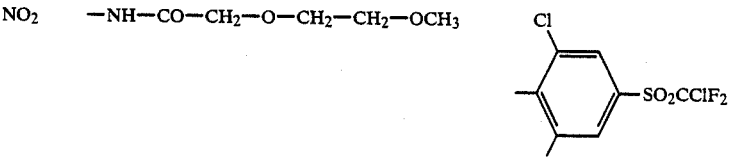 |
| NO₂ | —NH—CO—CH₂—O—CH₂—CH₂—OCH₃ | 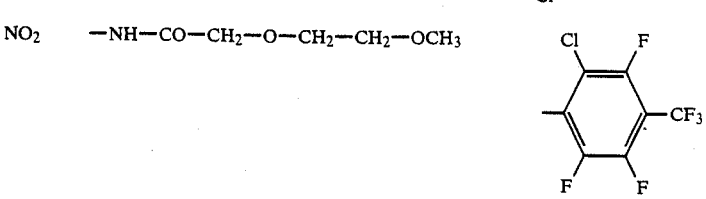 |

-continued

[Structure: pyrazole with N-Ar, R¹ at 4-position, N(R²)-C(O)-A¹-(O-A²)ₙ-Y at 5-position]

| R¹ | −N(R²)−C(O)−A¹−(O−A²)ₙ−Y | Ar |
|---|---|---|
| NO₂ | −NH−CO−CH₂−O−CH₂−CH₂−OCH₃ | 2,6-dichloro-3,5-difluoro-4-(CF₃)-phenyl |
| NO₂ | −NH−CO−CH₂−O−CH₂−CH₂−OCH₃ | 2,4,5-trichloro-3-fluoro-phenyl (Cl, F; Cl; Cl, F) |
| NO₂ | −NH−CO−CH₂−O−CH₂−CH₂−OCH₃ | 2,4-dichloro-3,5,6-trifluoro-phenyl-Cl |
| NO₂ | −NH−CO−CH₂−O−CH₂−CH₂−OCH₃ | 2-chloro-5,6-difluoro-4-(CF₃)-phenyl |
| NO₂ | −NH−CO−CH₂−O−CH₂−CH₂−OCH₃ | 5,6-dichloro-4-(CF₃)-phenyl |
| NO₂ | −NH−CO−CH₂−O−CH₂−CH₂−OCH₃ | 5-chloro-6-fluoro-4-(CF₃)-phenyl |
| NO₂ | −NH−CO−CH₂−O−CH₂−CH₂−OCH₃ | 2,5-dichloro-4-(CF₃)-phenyl |

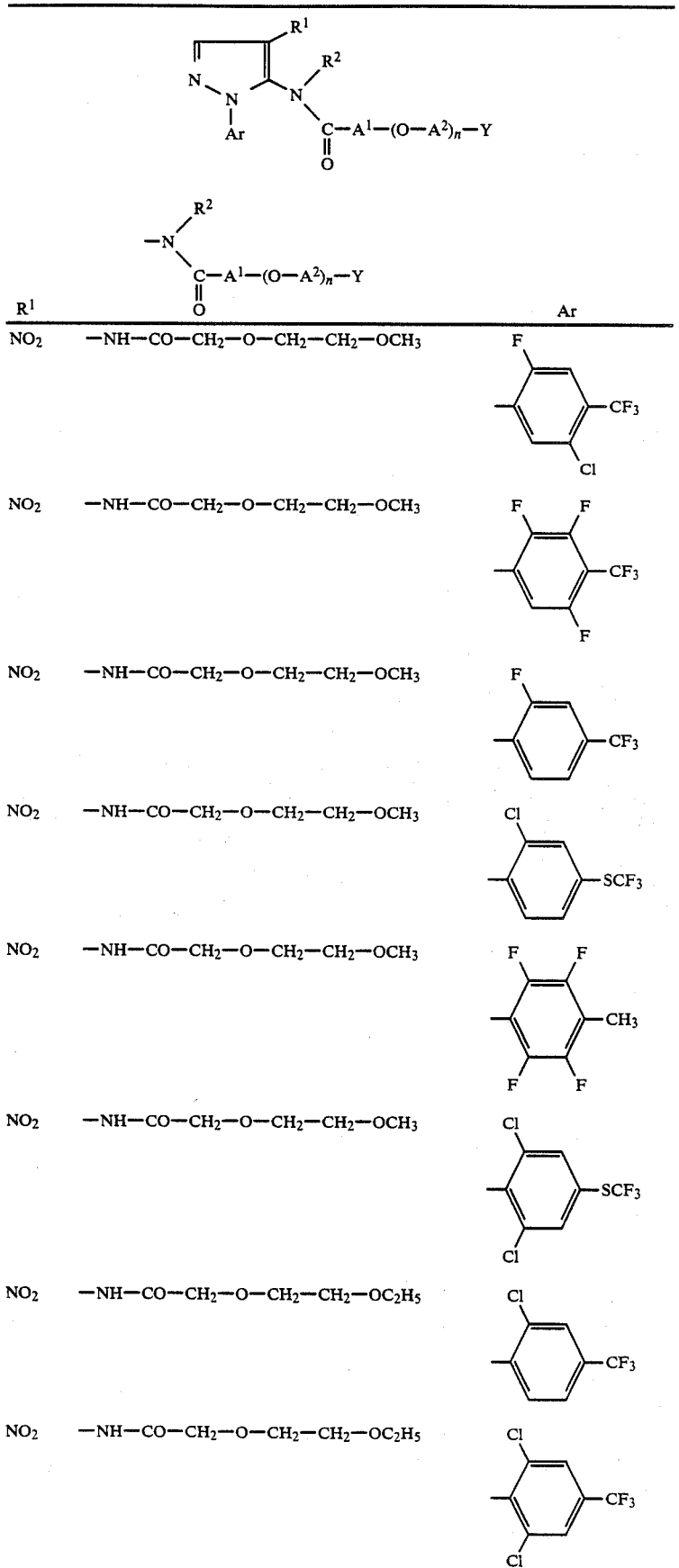

-continued
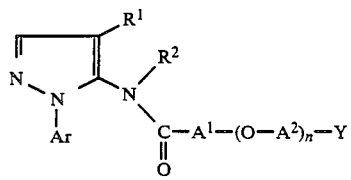
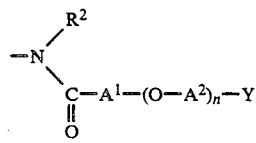
| R¹ | | Ar |
|---|---|---|
| NO₂ | —NH—CO—CH₂—O—CH₂—CH₂—OC₂H₅ | 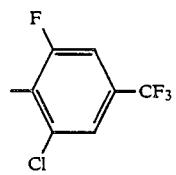 |
| NO₂ | —NH—CO—CH₂—O—CH₂—CH₂—OC₂H₅ | 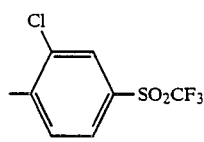 |
| NO₂ | —NH—CO—CH₂—O—CH₂—CH₂—OC₂H₅ | 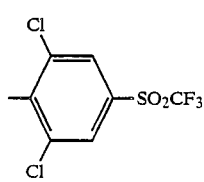 |
| NO₂ | —NH—CO—CH₂—O—CH₂—CH₂—OC₂H₅ | 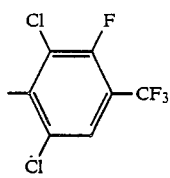 |
| NO₂ | —NH—CO—CH₂—O—CH₂—CH₂—OC₂H₅ | 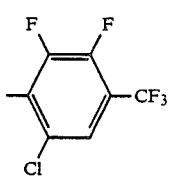 |
| NO₂ | —NH—CO—CH₂—O—CH₂—CH₂—OC₂H₅ | 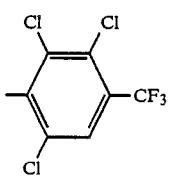 |
| NO₂ | —NH—CO—CH₂—O—CH₂—CH₂—OC₂H₅ | 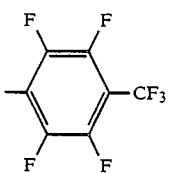 |

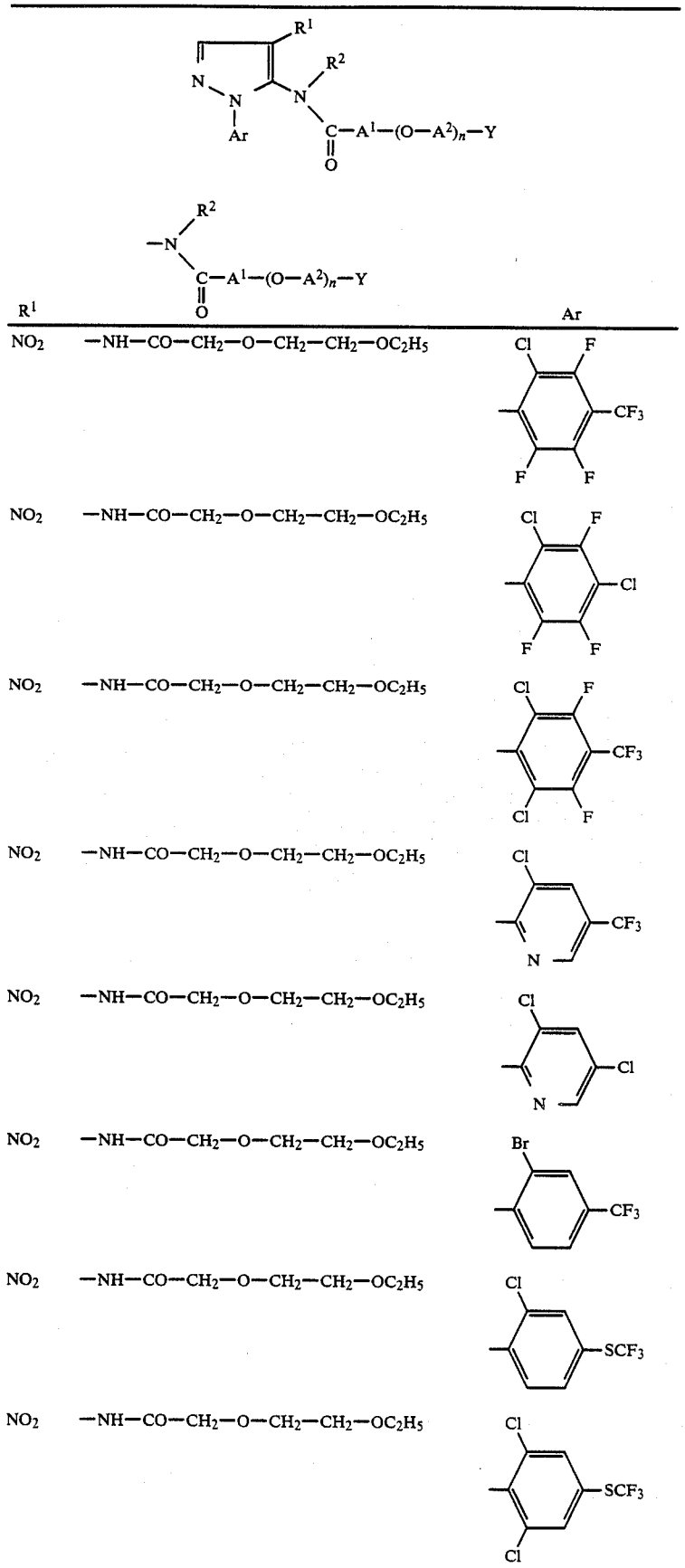

-continued
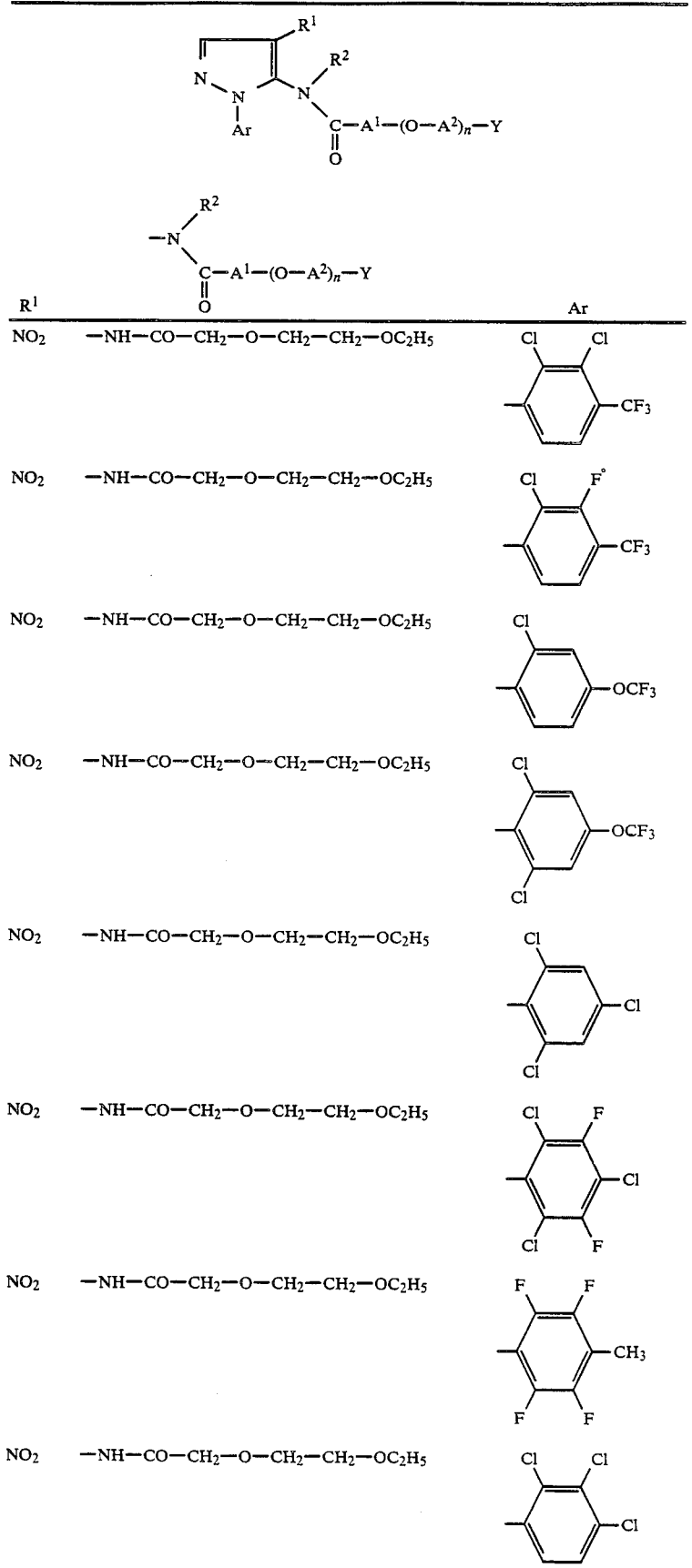
| $R^1$ | (group) | Ar |
|---|---|---|
| $NO_2$ | $-NH-CO-CH_2-O-CH_2-CH_2-OC_2H_5$ | 2,3-Cl$_2$-4-CF$_3$-phenyl |
| $NO_2$ | $-NH-CO-CH_2-O-CH_2-CH_2-OC_2H_5$ | 2-Cl-3-F-4-CF$_3$-phenyl |
| $NO_2$ | $-NH-CO-CH_2-O-CH_2-CH_2-OC_2H_5$ | 2-Cl-4-OCF$_3$-phenyl |
| $NO_2$ | $-NH-CO-CH_2-O-CH_2-CH_2-OC_2H_5$ | 2,5-Cl$_2$-4-OCF$_3$-phenyl |
| $NO_2$ | $-NH-CO-CH_2-O-CH_2-CH_2-OC_2H_5$ | 2,4,5-Cl$_3$-phenyl |
| $NO_2$ | $-NH-CO-CH_2-O-CH_2-CH_2-OC_2H_5$ | 2,4-Cl$_2$-3,5-F$_2$-phenyl |
| $NO_2$ | $-NH-CO-CH_2-O-CH_2-CH_2-OC_2H_5$ | 2,3,5,6-F$_4$-4-CH$_3$-phenyl |
| $NO_2$ | $-NH-CO-CH_2-O-CH_2-CH_2-OC_2H_5$ | 2,3,4-Cl$_3$-phenyl |

-continued
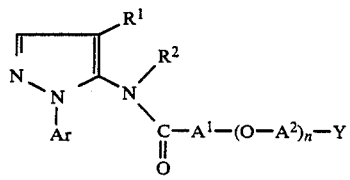
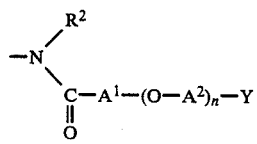
| $R^1$ | | Ar |
|---|---|---|
| $NO_2$ | $-NH-CO-CH_2-O-CH_2-CH_2-OC_2H_5$ | 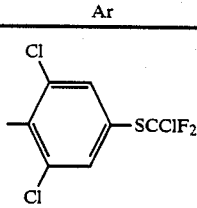 |
| $NO_2$ | $-NH-CO-CH_2-O-CH_2-CH_2-OC_4H_9-n$ | 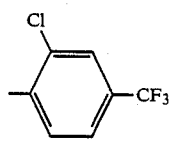 |
| $NO_2$ | $-NH-CO-CH_2-O-CH_2-CH_2-OC_4H_9-n$ | 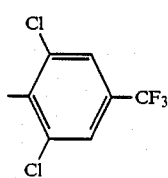 |
| $NO_2$ | $-NH-CO-CH_2-O-CH_2-CH_2-OC_4H_9-n$ | 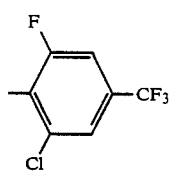 |
| $NO_2$ | $-NH-CO-CH_2-O-CH_2-CH_2-OC_4H_9-n$ | 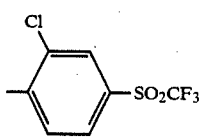 |
| $NO_2$ | $-NH-CO-CH_2-O-CH_2-CH_2-OC_4H_9-n$ | 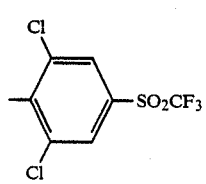 |
| $NO_2$ | $-NH-CO-CH_2-O-CH_2-CH_2-OC_4H_9-n$ | 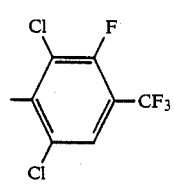 |

-continued

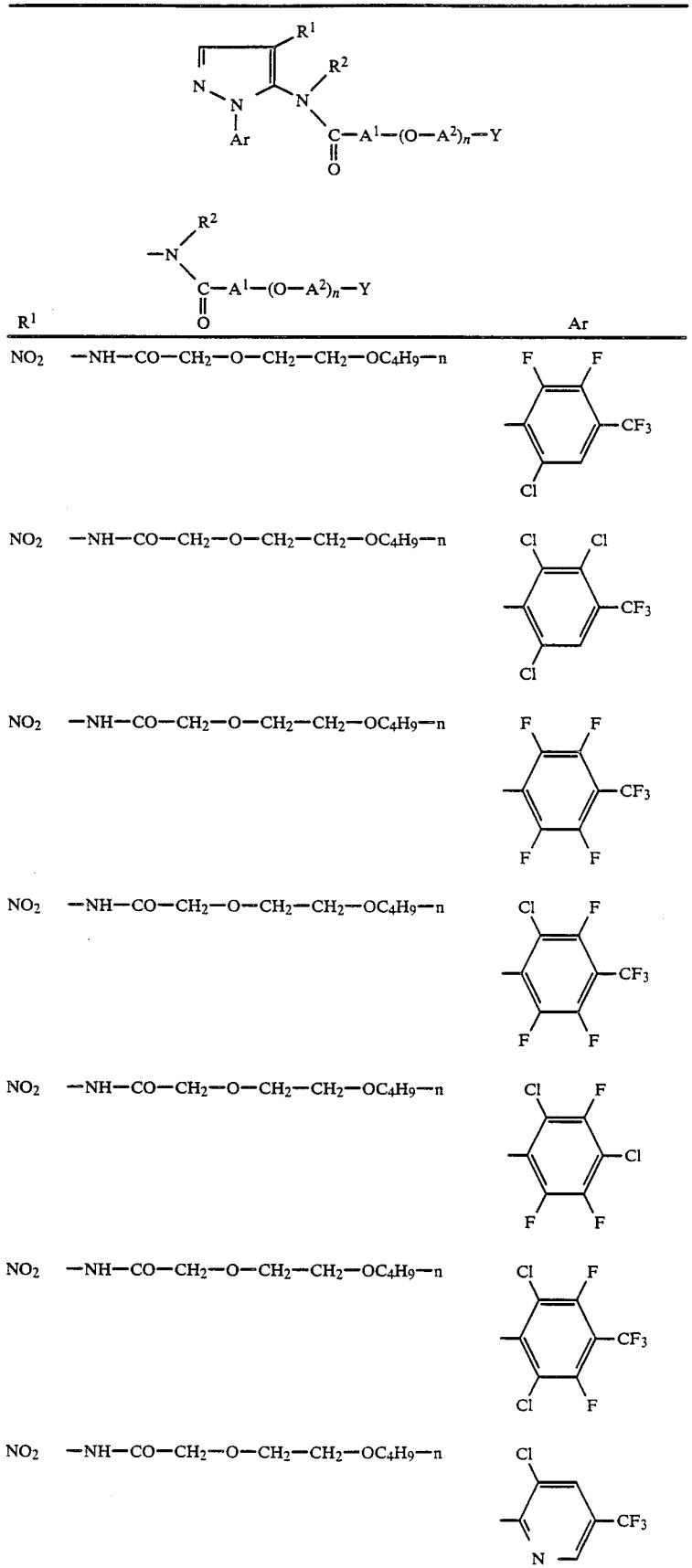

| R¹ | −N(R²)−C(O)−A¹−(O−A²)ₙ−Y | Ar |
|---|---|---|
| NO₂ | −NH−CO−CH₂−O−CH₂−CH₂−OC₄H₉-n | 2,3-F₂-4-CF₃-6-Cl-phenyl |
| NO₂ | −NH−CO−CH₂−O−CH₂−CH₂−OC₄H₉-n | 2,3,6-Cl₃-4-CF₃-phenyl |
| NO₂ | −NH−CO−CH₂−O−CH₂−CH₂−OC₄H₉-n | 2,3,5,6-F₄-4-CF₃-phenyl |
| NO₂ | −NH−CO−CH₂−O−CH₂−CH₂−OC₄H₉-n | 2-Cl-3,5,6-F₃-4-CF₃-phenyl* |
| NO₂ | −NH−CO−CH₂−O−CH₂−CH₂−OC₄H₉-n | 2-Cl-3,6-F₂-4-CF₃-5-Cl-phenyl* |
| NO₂ | −NH−CO−CH₂−O−CH₂−CH₂−OC₄H₉-n | 2-Cl-3-F-4-CF₃-5-F-6-Cl-phenyl* |
| NO₂ | −NH−CO−CH₂−O−CH₂−CH₂−OC₄H₉-n | 3-Cl-5-CF₃-pyridin-2-yl |

-continued

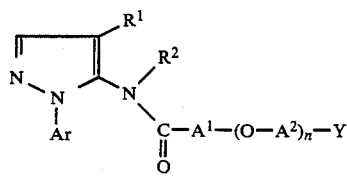

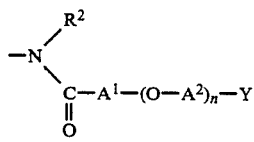

| R¹ | —N(R²)—C(O)—A¹—(O—A²)ₙ—Y | Ar |
|---|---|---|
| NO₂ | —NH—CO—CH₂—O—CH₂—CH₂—OC₄H₉-n | 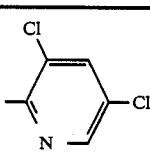 3,5-dichloropyridin-2-yl |
| NO₂ | —NH—CO—CH₂—O—CH₂—CH₂—OC₄H₉-n | 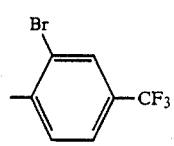 2-Br, 4-CF₃ phenyl |
| NO₂ | —NH—CO—CH₂—O—CH₂—CH₂—OC₄H₉-n | 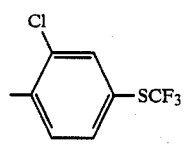 2-Cl, 4-SCF₃ phenyl |
| NO₂ | —NH—CO—CH₂—O—CH₂—CH₂—OC₄H₉-n | 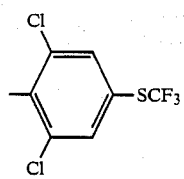 2,5-diCl, 4-SCF₃ phenyl |
| NO₂ | —NH—CO—CH₂—O—CH₂—CH₂—OC₄H₉-n | 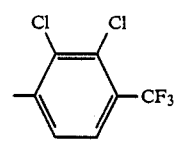 2,3-diCl, 4-CF₃ phenyl |
| NO₂ | —NH—CO—CH₂—O—CH₂—CH₂—OC₄H₉-n | 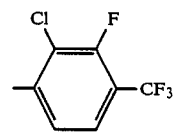 2-Cl, 3-F, 4-CF₃ phenyl |
| NO₂ | —NH—CO—CH₂—O—CH₂—CH₂—OC₄H₉-n | 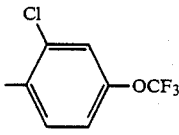 2-Cl, 4-OCF₃ phenyl |
| NO₂ | —NH—CO—CH₂—O—CH₂—CH₂—OC₄H₉-n | 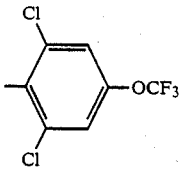 2,5-diCl, 4-OCF₃ phenyl |

-continued

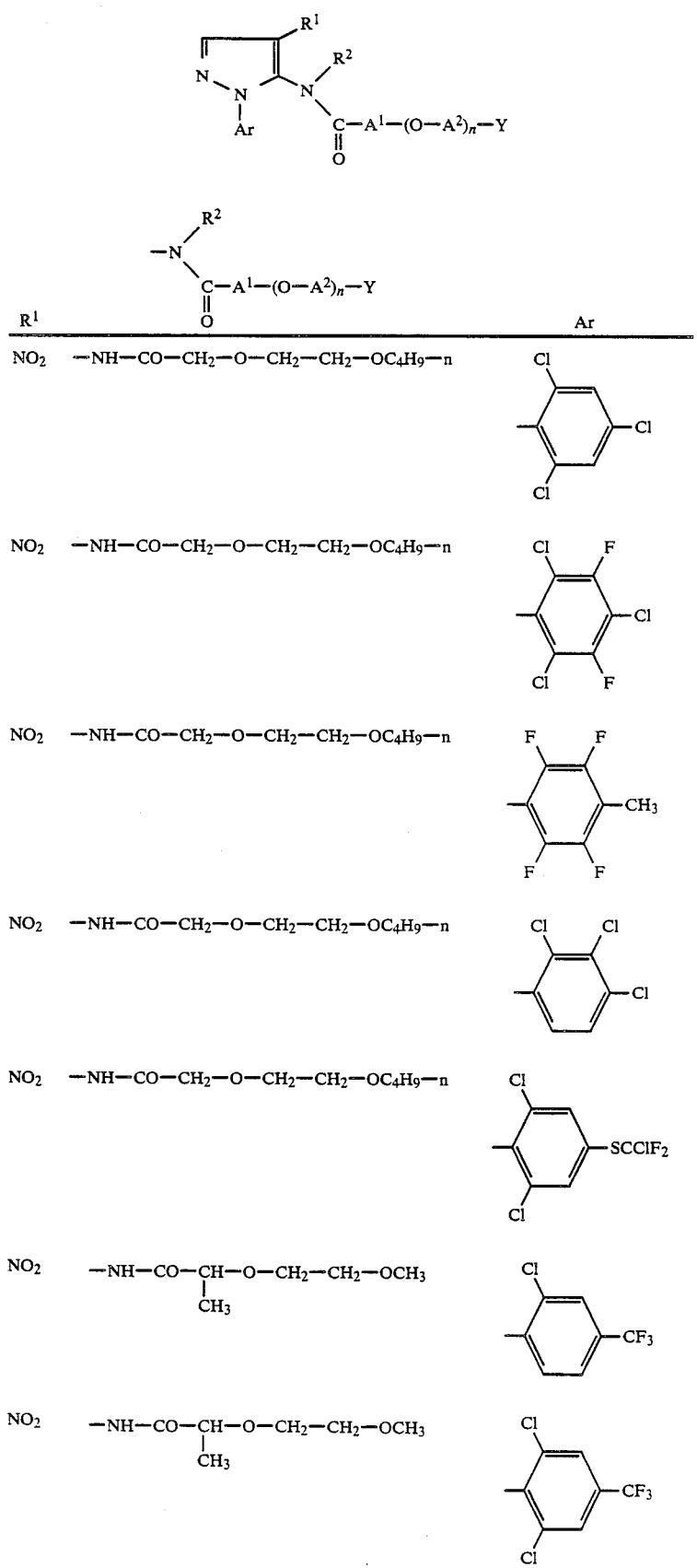

| $R^1$ | structure | Ar |
|---|---|---|
| $NO_2$ | $-NH-CO-CH_2-O-CH_2-CH_2-OC_4H_9-n$ | 2,4,6-trichlorophenyl |
| $NO_2$ | $-NH-CO-CH_2-O-CH_2-CH_2-OC_4H_9-n$ | 2,4-dichloro-3,5-difluorophenyl |
| $NO_2$ | $-NH-CO-CH_2-O-CH_2-CH_2-OC_4H_9-n$ | 2,3,5,6-tetrafluoro-4-methylphenyl |
| $NO_2$ | $-NH-CO-CH_2-O-CH_2-CH_2-OC_4H_9-n$ | 2,3,4-trichlorophenyl |
| $NO_2$ | $-NH-CO-CH_2-O-CH_2-CH_2-OC_4H_9-n$ | 2,6-dichloro-4-(SCClF$_2$)phenyl |
| $NO_2$ | $-NH-CO-CH(CH_3)-O-CH_2-CH_2-OCH_3$ | 2-chloro-4-trifluoromethylphenyl |
| $NO_2$ | $-NH-CO-CH(CH_3)-O-CH_2-CH_2-OCH_3$ | 2,5-dichloro-4-trifluoromethylphenyl |

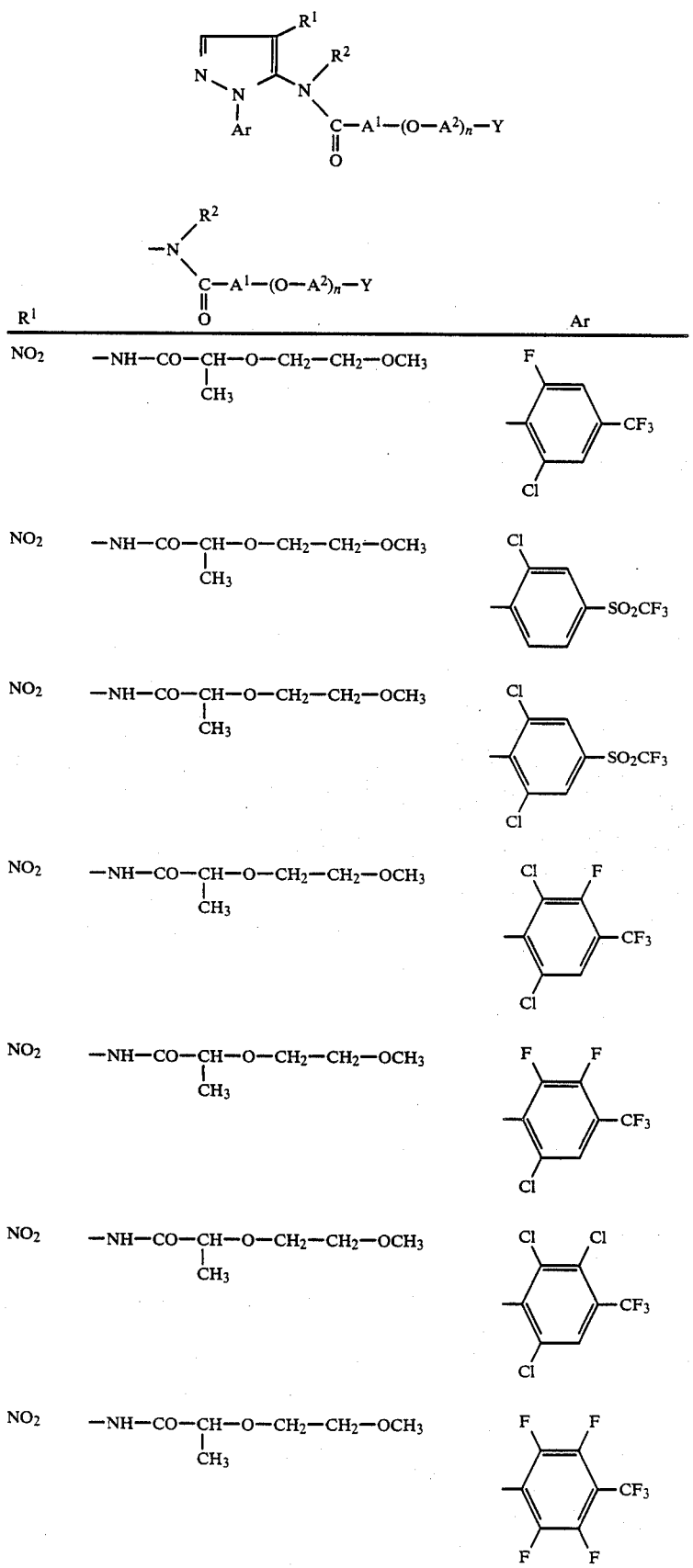

-continued

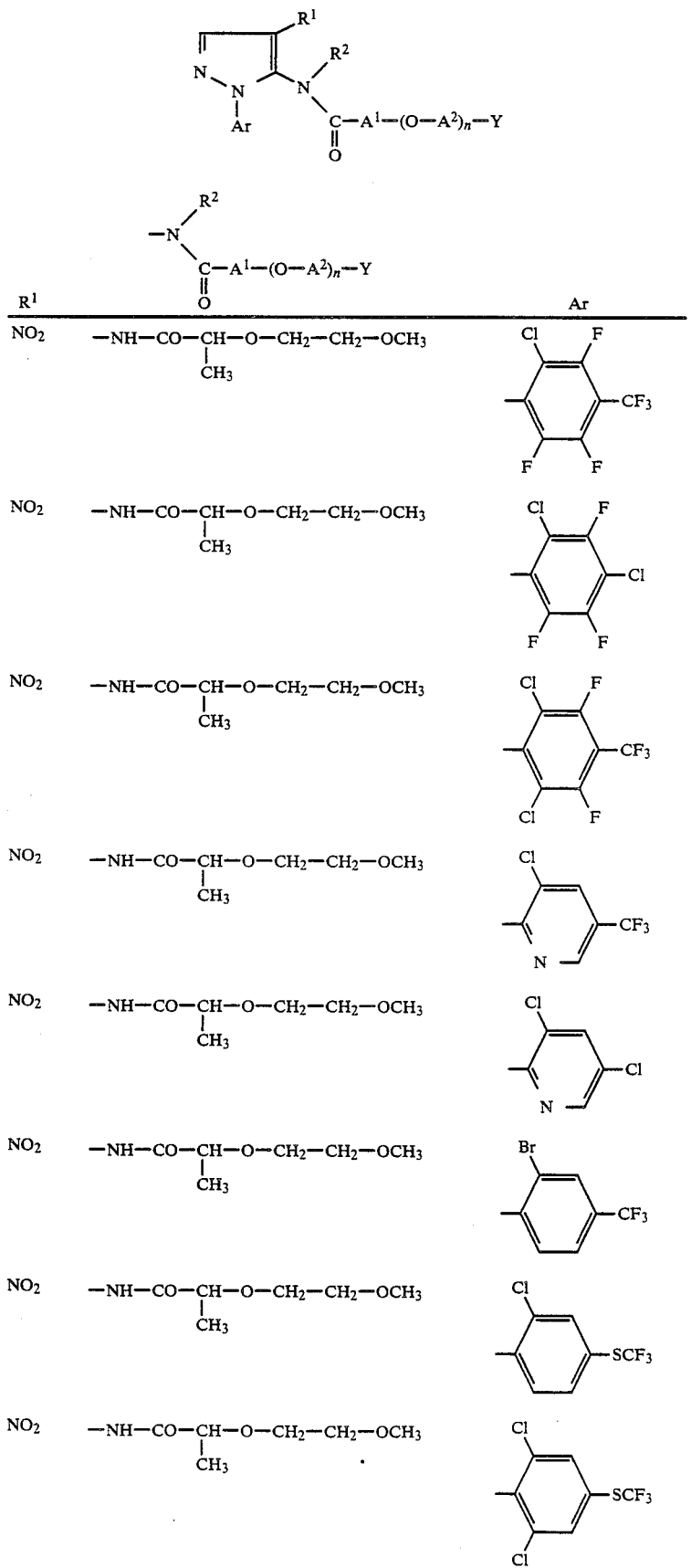

| R¹ | —N(R²)—CO—A¹—(O—A²)ₙ—Y | Ar |
|---|---|---|
| NO₂ | —NH—CO—CH(CH₃)—O—CH₂—CH₂—OCH₃ | 2-Cl, 3-F, 4-CF₃, 5-F, 6-F phenyl |
| NO₂ | —NH—CO—CH(CH₃)—O—CH₂—CH₂—OCH₃ | 2-Cl, 3-F, 4-Cl, 5-F, 6-F phenyl |
| NO₂ | —NH—CO—CH(CH₃)—O—CH₂—CH₂—OCH₃ | 2-Cl, 3-F, 4-CF₃, 5-F, 6-Cl phenyl |
| NO₂ | —NH—CO—CH(CH₃)—O—CH₂—CH₂—OCH₃ | 3-Cl, 5-CF₃ pyridin-2-yl |
| NO₂ | —NH—CO—CH(CH₃)—O—CH₂—CH₂—OCH₃ | 3-Cl, 5-Cl pyridin-2-yl |
| NO₂ | —NH—CO—CH(CH₃)—O—CH₂—CH₂—OCH₃ | 2-Br, 4-CF₃ phenyl |
| NO₂ | —NH—CO—CH(CH₃)—O—CH₂—CH₂—OCH₃ | 2-Cl, 4-SCF₃ phenyl |
| NO₂ | —NH—CO—CH(CH₃)—O—CH₂—CH₂—OCH₃ | 2-Cl, 4-SCF₃, 6-Cl phenyl |

-continued

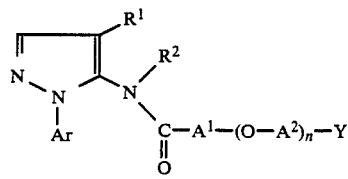

| R¹ | —N(R²)—CO—A¹—(O—A²)ₙ—Y | Ar |
|---|---|---|
| NO₂ | —NH—CO—CH(CH₃)—O—CH₂—CH₂—OCH₃ | 2,3-Cl₂-4-CF₃-phenyl |
| NO₂ | —NH—CO—CH(CH₃)—O—CH₂—CH₂—OCH₃ | 2-Cl-3-F-4-CF₃-phenyl |
| NO₂ | —NH—CO—CH(CH₃)—O—CH₂—CH₂—OCH₃ | 2-Cl-4-OCF₃-phenyl |
| NO₂ | —NH—CO—CH(CH₃)—O—CH₂—CH₂—OCH₃ | 2,6-Cl₂-4-OCF₃-phenyl |
| NO₂ | —NH—CO—CH(CH₃)—O—CH₂—CH₂—OCH₃ | 2,4,6-Cl₃-phenyl |
| NO₂ | —NH—CO—CH(CH₃)—O—CH₂—CH₂—OCH₃ | 2,4-Cl₂-3,5,6-F₂-... (2,4-Cl₂-3,6-F₂-phenyl) |
| NO₂ | —NH—CO—CH(CH₃)—O—CH₂—CH₂—OCH₃ | 2,3,5,6-F₄-4-CH₃-phenyl |
| NO₂ | —NH—CO—CH(CH₃)—O—CH₂—CH₂—OCH₃ | 2,3-Cl₂-phenyl |

-continued

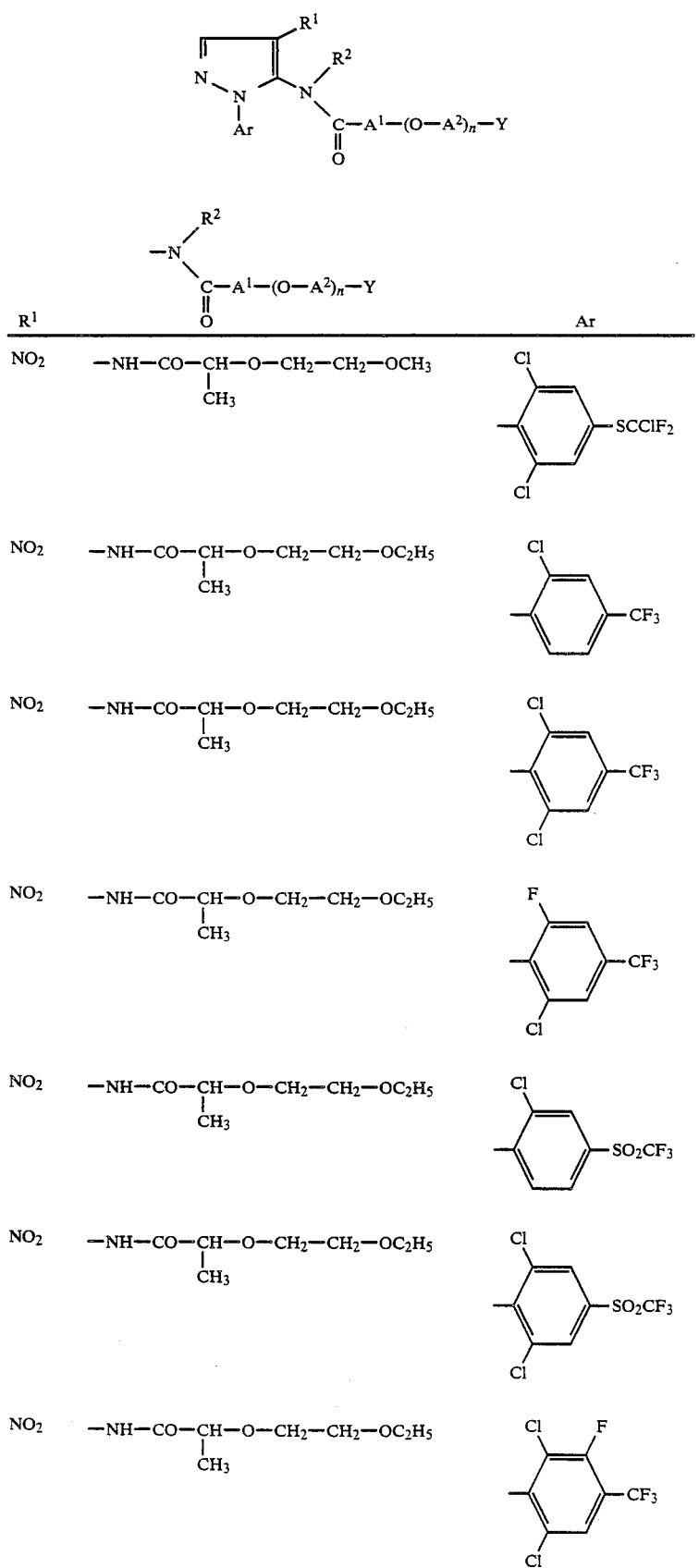

| R¹ | | Ar |
|---|---|---|
| NO₂ | —NH—CO—CH(CH₃)—O—CH₂—CH₂—OCH₃ | 3,5-dichloro-4-(SCClF₂)phenyl |
| NO₂ | —NH—CO—CH(CH₃)—O—CH₂—CH₂—OC₂H₅ | 2-chloro-4-(CF₃)phenyl |
| NO₂ | —NH—CO—CH(CH₃)—O—CH₂—CH₂—OC₂H₅ | 2,6-dichloro-4-(CF₃)phenyl |
| NO₂ | —NH—CO—CH(CH₃)—O—CH₂—CH₂—OC₂H₅ | 2-fluoro-6-chloro-4-(CF₃)phenyl |
| NO₂ | —NH—CO—CH(CH₃)—O—CH₂—CH₂—OC₂H₅ | 2-chloro-4-(SO₂CF₃)phenyl |
| NO₂ | —NH—CO—CH(CH₃)—O—CH₂—CH₂—OC₂H₅ | 2,6-dichloro-4-(SO₂CF₃)phenyl |
| NO₂ | —NH—CO—CH(CH₃)—O—CH₂—CH₂—OC₂H₅ | 2,6-dichloro-3-fluoro-4-(CF₃)phenyl |

-continued
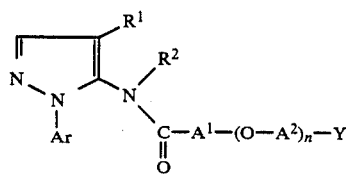
| R¹ | 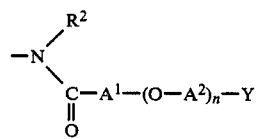 | Ar |
|---|---|---|
| $NO_2$ | $-NH-CO-CH(CH_3)-O-CH_2-CH_2-OC_2H_5$ | 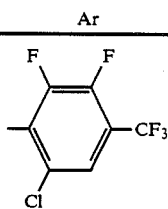 |
| $NO_2$ | $-NH-CO-CH(CH_3)-O-CH_2-CH_2-OC_2H_5$ | 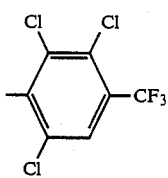 |
| $NO_2$ | $-NH-CO-CH(CH_3)-O-CH_2-CH_2-OC_2H_5$ | 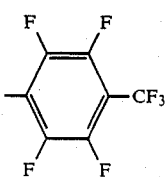 |
| $NO_2$ | $-NH-CO-CH(CH_3)-O-CH_2-CH_2-OC_2H_5$ | 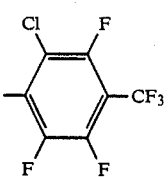 |
| $NO_2$ | $-NH-CO-CH(CH_3)-O-CH_2-CH_2-OC_2H_5$ | 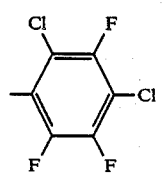 |
| $NO_2$ | $-NH-CO-CH(CH_3)-O-CH_2-CH_2-OC_2H_5$ | 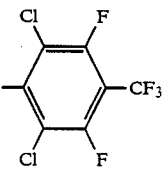 |
| $NO_2$ | $-NH-CO-CH(CH_3)-O-CH_2-CH_2-OC_2H_5$ | 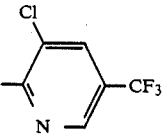 |

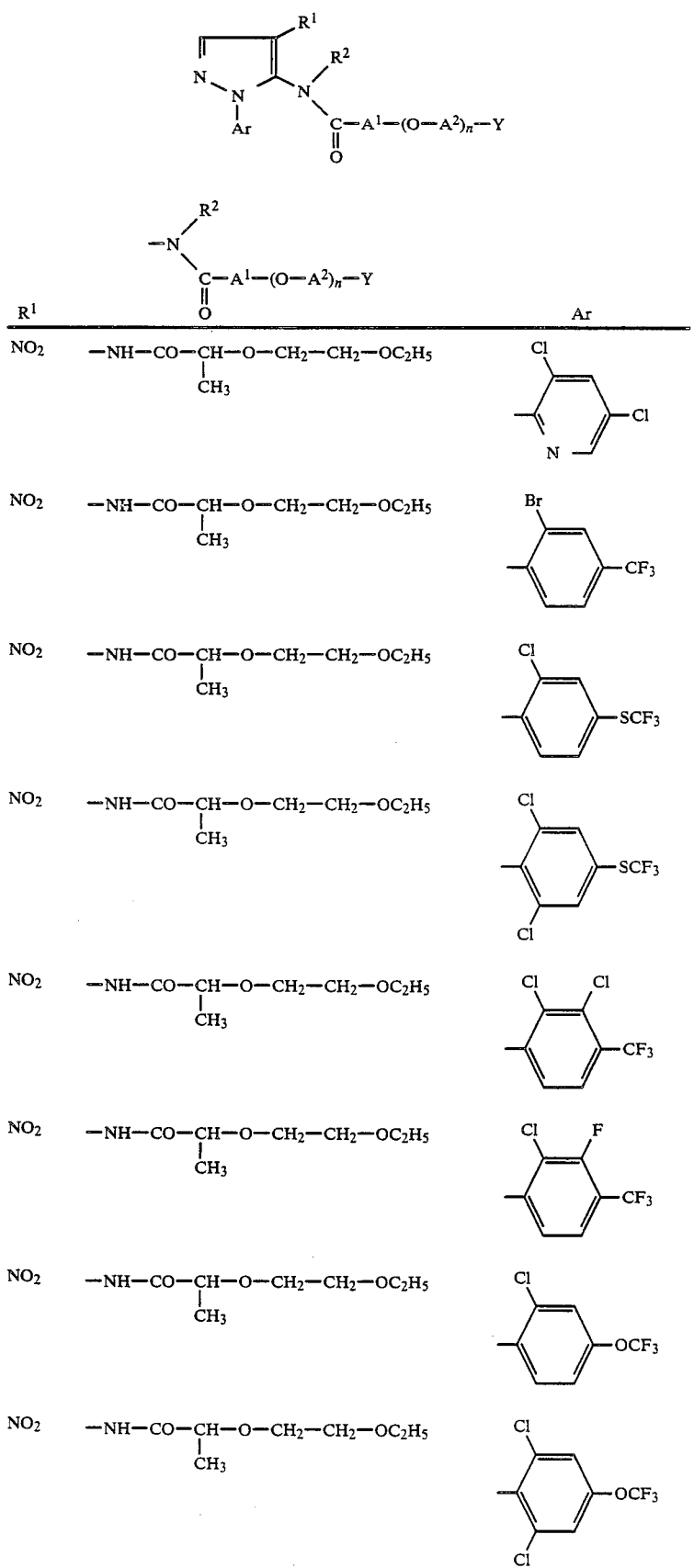

-continued

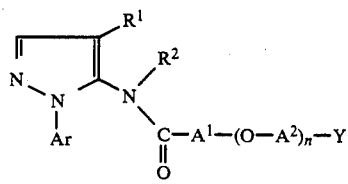

| R¹ | —N(R²)—CO—A¹—(O—A²)ₙ—Y | Ar |
|---|---|---|
| NO₂ | —NH—CO—CH(CH₃)—O—CH₂—CH₂—OC₂H₅ | 2,4,6-trichlorophenyl |
| NO₂ | —NH—CO—CH(CH₃)—O—CH₂—CH₂—OC₂H₅ | 2,6-dichloro-3,5-difluorophenyl |
| NO₂ | —NH—CO—CH(CH₃)—O—CH₂—CH₂—OC₂H₅ | 4-methyl-2,3,5,6-tetrafluorophenyl |
| NO₂ | —NH—CO—CH(CH₃)—O—CH₂—CH₂—OC₂H₅ | 2,3,4-trichlorophenyl |
| NO₂ | —NH—CO—CH(CH₃)—O—CH₂—CH₂—OC₂H₅ | 2,6-dichloro-4-(SCClF₂)phenyl |
| NO₂ | —NH—CO—CH(C₂H₅)—O—CH₂—CH₂—OCH₃ | 2-chloro-4-(CF₃)phenyl |
| NO₂ | —NH—CO—CH(C₂H₅)—O—CH₂—CH₂—OCH₃ | 2,6-dichloro-4-(CF₃)phenyl |

-continued

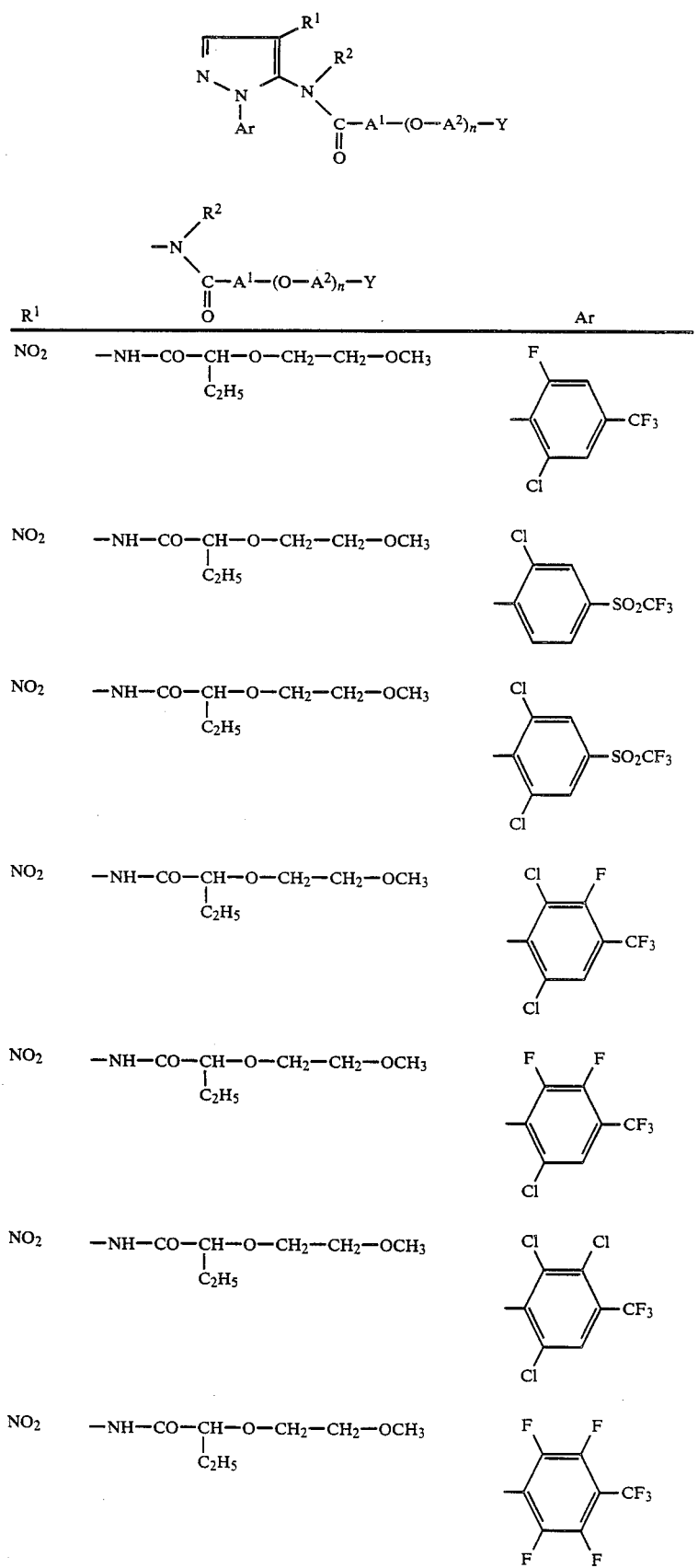

| $R^1$ | —N(R²)—CO—$A^1$—(O—$A^2$)$_n$—Y | Ar |
|---|---|---|
| $NO_2$ | —NH—CO—CH(C₂H₅)—O—CH₂—CH₂—OCH₃ | 2-F, 3-Cl, 4-(point), 5-CF₃ phenyl (F, Cl, CF₃ substituted) |
| $NO_2$ | —NH—CO—CH(C₂H₅)—O—CH₂—CH₂—OCH₃ | 2-Cl, 4-SO₂CF₃ phenyl |
| $NO_2$ | —NH—CO—CH(C₂H₅)—O—CH₂—CH₂—OCH₃ | 2,6-diCl, 4-SO₂CF₃ phenyl |
| $NO_2$ | —NH—CO—CH(C₂H₅)—O—CH₂—CH₂—OCH₃ | 2-Cl, 3-F, 5-Cl, 4-CF₃ phenyl |
| $NO_2$ | —NH—CO—CH(C₂H₅)—O—CH₂—CH₂—OCH₃ | 2,3-diF, 5-Cl, 4-CF₃ phenyl |
| $NO_2$ | —NH—CO—CH(C₂H₅)—O—CH₂—CH₂—OCH₃ | 2,3,5-triCl, 4-CF₃ phenyl |
| $NO_2$ | —NH—CO—CH(C₂H₅)—O—CH₂—CH₂—OCH₃ | 2,3,5,6-tetraF, 4-CF₃ phenyl |

-continued
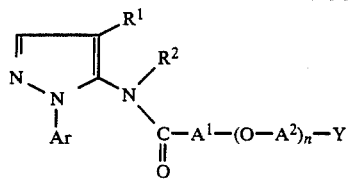
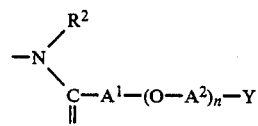
| R¹ | (substituent column) | Ar |
|---|---|---|
| NO₂ | —NH—CO—CH(C₂H₅)—O—CH₂—CH₂—OCH₃ | 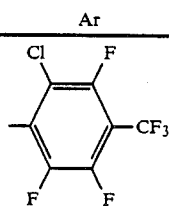 |
| NO₂ | —NH—CO—CH(C₂H₅)—O—CH₂—CH₂—OCH₃ | 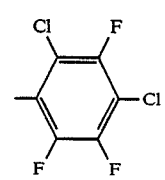 |
| NO₂ | —NH—CO—CH(C₂H₅)—O—CH₂—CH₂—OCH₃ | 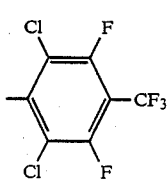 |
| NO₂ | —NH—CO—CH(C₂H₅)—O—CH₂—CH₂—OCH₃ | 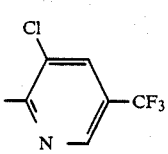 |
| NO₂ | —NH—CO—CH(C₂H₅)—O—CH₂—CH₂—OCH₃ | 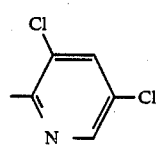 |
| NO₂ | —NH—CO—CH(C₂H₅)—O—CH₂—CH₂—OCH₃ | 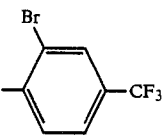 |
| NO₂ | —NH—CO—CH(C₂H₅)—O—CH₂—CH₂—OCH₃ | 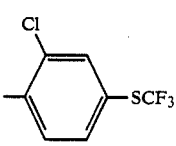 |
| NO₂ | —NH—CO—CH(C₂H₅)—O—CH₂—CH₂—OCH₃ | 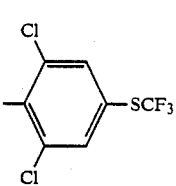 |

-continued

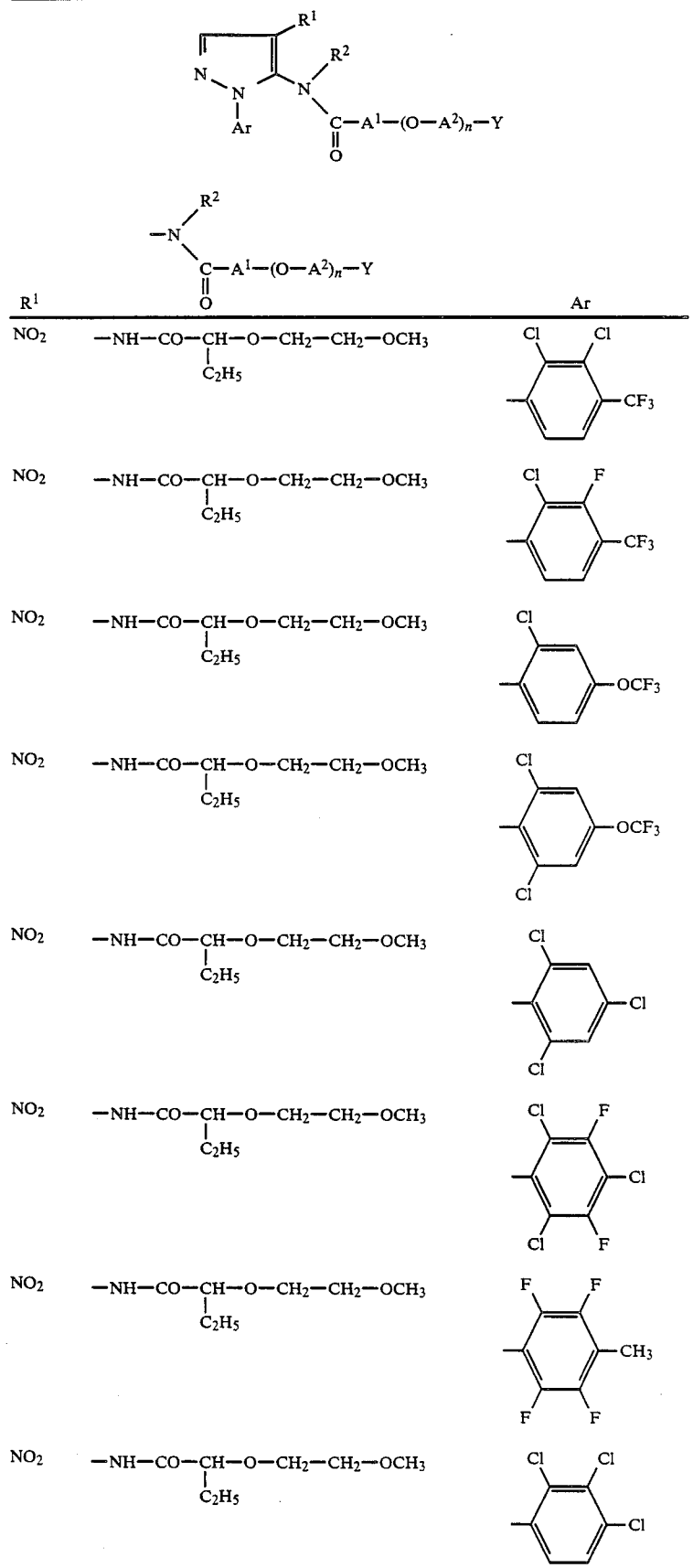

| R¹ | | Ar |
|---|---|---|
| NO₂ | —NH—CO—CH—O—CH₂—CH₂—OCH₃<br>　　　　　\|<br>　　　　　C₂H₅ | 2,3-Cl₂-4-CF₃-phenyl |
| NO₂ | —NH—CO—CH—O—CH₂—CH₂—OCH₃<br>　　　　　\|<br>　　　　　C₂H₅ | 2-Cl-3-F-4-CF₃-phenyl |
| NO₂ | —NH—CO—CH—O—CH₂—CH₂—OCH₃<br>　　　　　\|<br>　　　　　C₂H₅ | 2-Cl-4-OCF₃-phenyl |
| NO₂ | —NH—CO—CH—O—CH₂—CH₂—OCH₃<br>　　　　　\|<br>　　　　　C₂H₅ | 2,5-Cl₂-4-OCF₃-phenyl |
| NO₂ | —NH—CO—CH—O—CH₂—CH₂—OCH₃<br>　　　　　\|<br>　　　　　C₂H₅ | 2,4,6-Cl₃-phenyl |
| NO₂ | —NH—CO—CH—O—CH₂—CH₂—OCH₃<br>　　　　　\|<br>　　　　　C₂H₅ | 2,4-Cl₂-3,5,6-F₃-phenyl |
| NO₂ | —NH—CO—CH—O—CH₂—CH₂—OCH₃<br>　　　　　\|<br>　　　　　C₂H₅ | 2,3,5,6-F₄-4-CH₃-phenyl |
| NO₂ | —NH—CO—CH—O—CH₂—CH₂—OCH₃<br>　　　　　\|<br>　　　　　C₂H₅ | 2,3,6-Cl₃-phenyl |

-continued

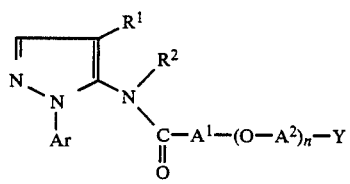

| $R^1$ | $-N\overset{R^2}{\underset{|}{-}}C-A^1-(O-A^2)_n-Y$ | Ar |
|---|---|---|
| NO₂ | −NH−CO−CH(C₂H₅)−O−CH₂−CH₂−OCH₃ | 2,6-dichloro-4-(SCClF₂)phenyl |
| NO₂ | −NH−CO−CH₂−CH₂−O−CH₂−CH₂−OCH₃ | 2-chloro-4-(CF₃)phenyl |
| NO₂ | −NH−CO−CH₂−CH₂−O−CH₂−CH₂−OCH₃ | 2,6-dichloro-4-(CF₃)phenyl |
| NO₂ | −NH−CO−CH₂−CH₂−O−CH₂−CH₂−OCH₃ | 2-fluoro-6-chloro-4-(CF₃)phenyl |
| NO₂ | −NH−CO−CH₂−CH₂−O−CH₂−CH₂−OCH₃ | 2-chloro-4-(SO₂CF₃)phenyl |
| NO₂ | −NH−CO−CH₂−CH₂−O−CH₂−CH₂−OCH₃ | 2,6-dichloro-4-(SO₂CF₃)phenyl |
| NO₂ | −NH−CO−CH₂−CH₂−O−CH₂−CH₂−OCH₃ | 2-chloro-6-fluoro-4-(CF₃)-5-chlorophenyl |

-continued
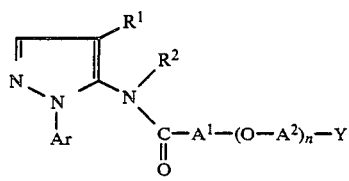
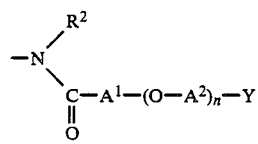
| R¹ | | Ar |
|---|---|---|
| NO₂ | —NH—CO—CH₂—CH₂—O—CH₂—CH₂—OCH₃ | 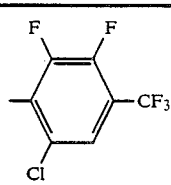 |
| NO₂ | —NH—CO—CH₂—CH₂—O—CH₂—CH₂—OCH₃ | 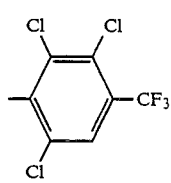 |
| NO₂ | —NH—CO—CH₂—CH₂—O—CH₂—CH₂—OCH₃ | 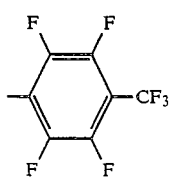 |
| NO₂ | —NH—CO—CH₂—CH₂—O—CH₂—CH₂—OCH₃ | 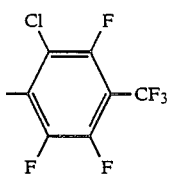 |
| NO₂ | —NH—CO—CH₂—CH₂—O—CH₂—CH₂—OCH₃ | 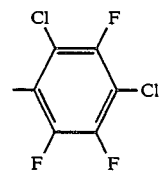 |
| NO₂ | —NH—CO—CH₂—CH₂—O—CH₂—CH₂—OCH₃ | 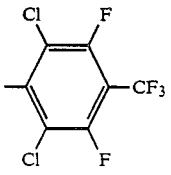 |
| NO₂ | —NH—CO—CH₂—CH₂—O—CH₂—CH₂—OCH₃ | 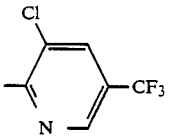 |

-continued

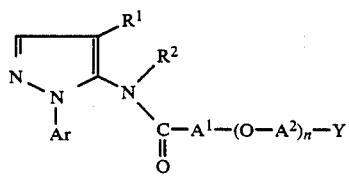

| $R^1$ | $-N\begin{smallmatrix}R^2\\|\end{smallmatrix}-C(=O)-A^1-(O-A^2)_n-Y$ | Ar |
|---|---|---|
| NO$_2$ | —NH—CO—CH(CH$_3$)—(O—CH$_2$—CH$_2$)$_2$—OCH$_3$ | 2-Cl, 4-CF$_3$-phenyl |
| NO$_2$ | —NH—CO—CH(CH$_3$)—(O—CH$_2$—CH$_2$)$_2$—OCH$_3$ | 2,6-Cl$_2$, 4-CF$_3$-phenyl |
| NO$_2$ | —NH—CO—CH(CH$_3$)—(O—CH$_2$—CH$_2$)$_2$—OCH$_3$ | 2-F, 6-Cl, 4-CF$_3$-phenyl |
| NO$_2$ | —NH—CO—CH(CH$_3$)—(O—CH$_2$—CH$_2$)$_2$—OCH$_3$ | 2-Cl, 4-SO$_2$CF$_3$-phenyl |
| NO$_2$ | —NH—CO—CH(CH$_3$)—(O—CH$_2$—CH$_2$)$_2$—OCH$_3$ | 2,6-Cl$_2$, 4-SO$_2$CF$_3$-phenyl |
| NO$_2$ | —NH—CO—CH(CH$_3$)—(O—CH$_2$—CH$_2$)$_2$—OCH$_3$ | 2-Cl, 6-F, 3-Cl, 4-CF$_3$-phenyl |
| NO$_2$ | —NH—CO—CH(CH$_3$)—(O—CH$_2$—CH$_2$)$_2$—OCH$_3$ | 2,6-F$_2$, 3-Cl, 4-CF$_3$-phenyl |

-continued

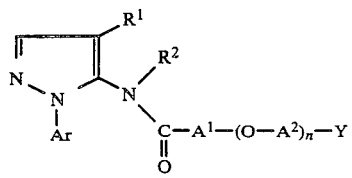

| R¹ | -N(R²)-CO-A¹-(O-A²)ₙ-Y | Ar |
|---|---|---|
| $NO_2$ | $-NH-CO-CH(CH_3)-(O-CH_2-CH_2)_2-OCH_3$ | 2,3,5-trichloro-6-(trifluoromethyl)phenyl |
| $NO_2$ | $-NH-CO-CH(CH_3)-(O-CH_2-CH_2)_2-OCH_3$ | 2,3,5,6-tetrafluoro-4-(trifluoromethyl)phenyl |
| $NO_2$ | $-NH-CO-CH(CH_3)-(O-CH_2-CH_2)_2-OCH_3$ | 2-chloro-3,5,6-trifluoro-4-(trifluoromethyl)phenyl |
| $NO_2$ | $-NH-CO-CH(CH_3)-(O-CH_2-CH_2)_2-OCH_3$ | 2,5-difluoro-4-chloro-6-(substituted)phenyl |
| $NO_2$ | $-NH-CO-CH(CH_3)-(O-CH_2-CH_2)_2-OCH_3$ | 2,6-dichloro-3,5-difluoro-4-(trifluoromethyl)phenyl |
| $NO_2$ | $-NH-CO-CH(CH_3)-(O-CH_2-CH_2)_2-OCH_3$ | 3-chloro-5-(trifluoromethyl)-2-pyridyl |
| $NO_2$ | $-NH-CO-CH_2-(O-CH_2-CH_2)_2-OC_2H_5$ | 2-chloro-4-(trifluoromethyl)phenyl |

-continued
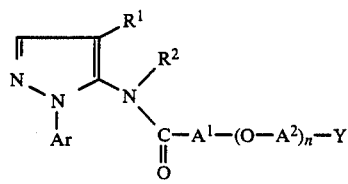
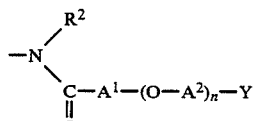
| $R^1$ | | Ar |
|---|---|---|
| $NO_2$ | $-NH-CO-CH_2-(O-CH_2-CH_2)_2-OC_2H_5$ | 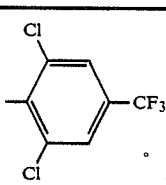 |
| $NO_2$ | $-NH-CO-CH_2-(O-CH_2-CH_2)_2-OC_2H_5$ | 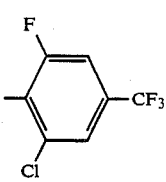 |
| $NO_2$ | $-NH-CO-CH_2-(O-CH_2-CH_2)_2-OC_2H_5$ | 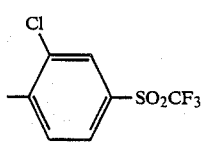 |
| $NO_2$ | $-NH-CO-CH_2-(O-CH_2-CH_2)_2-OC_2H_5$ | 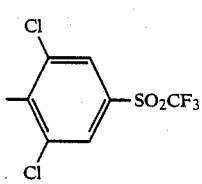 |
| $NO_2$ | $-NH-CO-CH_2-(O-CH_2-CH_2)_2-OC_2H_5$ | 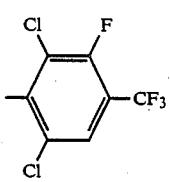 |
| $NO_2$ | $-NH-CO-CH_2-(O-CH_2-CH_2)_2-OC_2H_5$ | 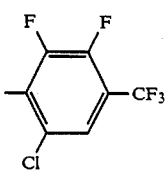 |
| $NO_2$ | $-NH-CO-CH_2-(O-CH_2-CH_2)_2-OC_2H_5$ | 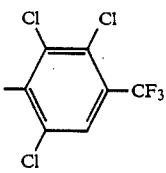 |

-continued
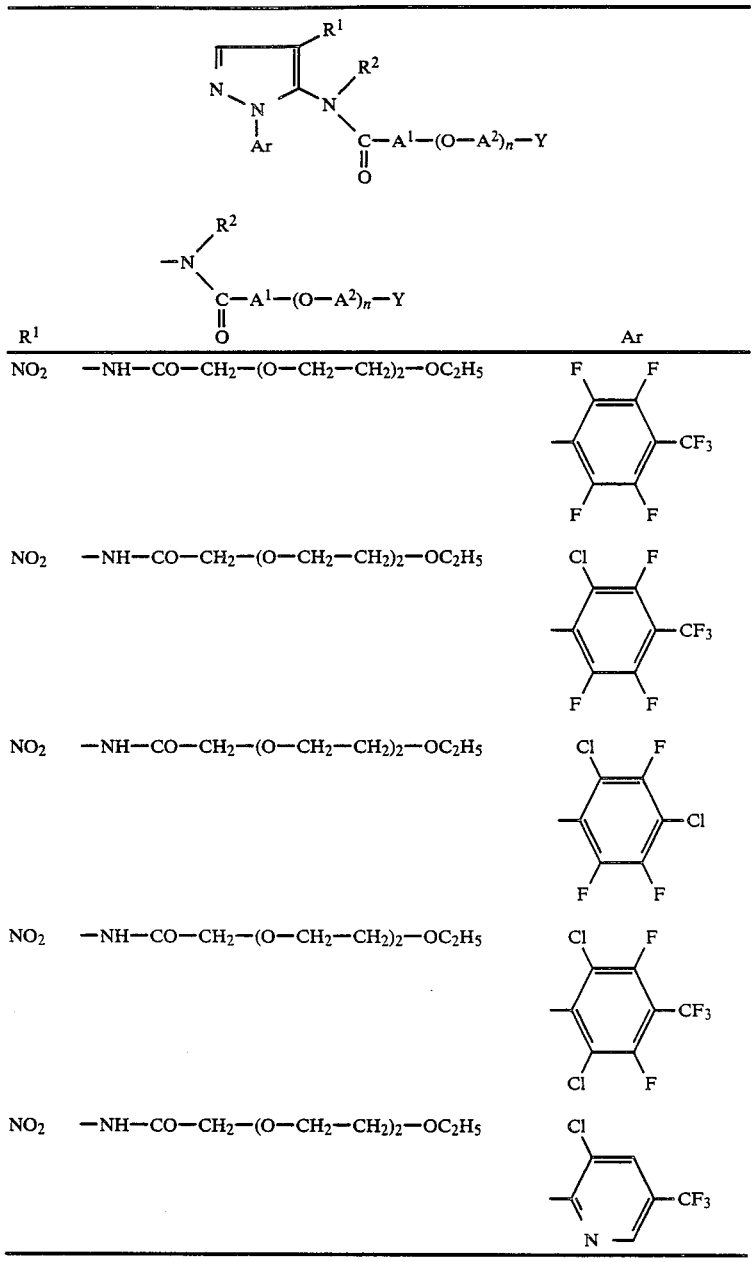
If, for example, 5-amino-4-nitro-1-(2,6-dichloro-4-trifluoromethylphenyl)-pyrazole and 2-methoxyethoxyacetyl chloride are used as starting substances, then the course of the reaction of process (a) according to the invention can be represented by the following equation:
-continued
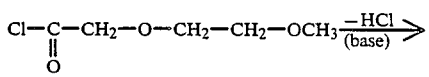
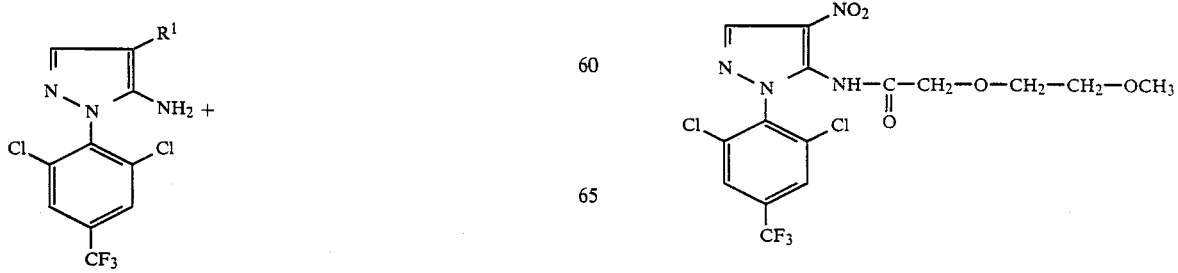

If, for example, 5-(2-methoxyethoxyacetamido)-4-nitro-1-(2,4,6-trichlorophenyl)-pyrazole and methyl iodide are used as starting substances, then the course of the reaction of process (b) according to the invention can be represented by the following equation:

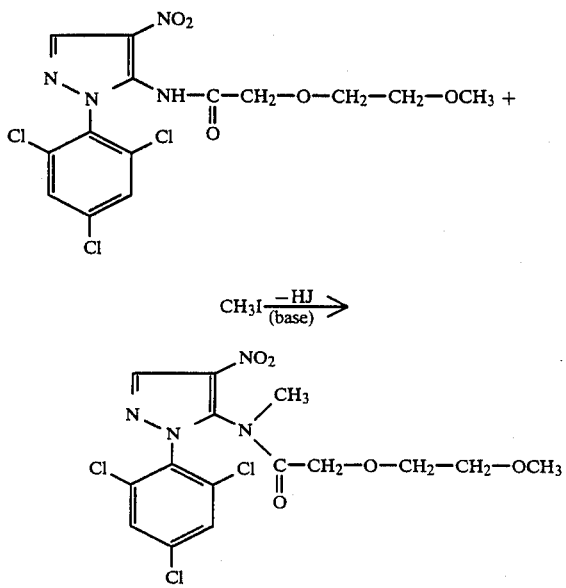

If, for example, 5-(2-ethoxyethoxyacetamido)-1-pentafluorophenyl-pyrazole is used as a starting compound, then the course of the reaction of process (c) according to the invention can be represented by the following equation:

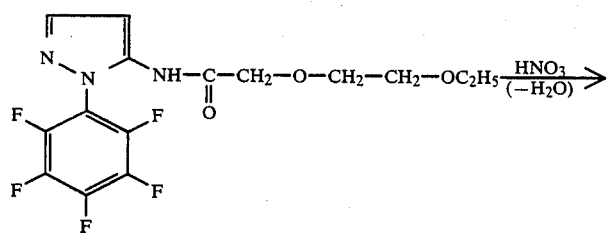

If, for example, 5-(2-hydroxyethoxyacetamido)-4-nitro-1-(2,3,6-trichloro-4-trifluoromethylphenyl)-pyrazole and propionyl chloride are used as starting substances, then the course of the reaction of process (d) according to the invention can be represented by the following equation:

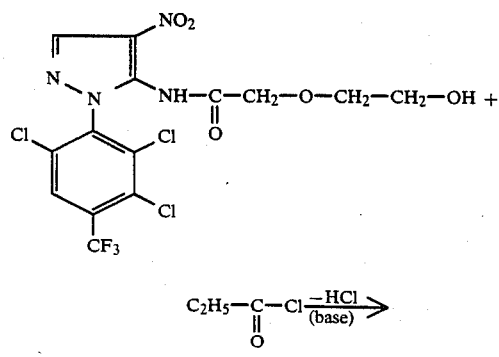

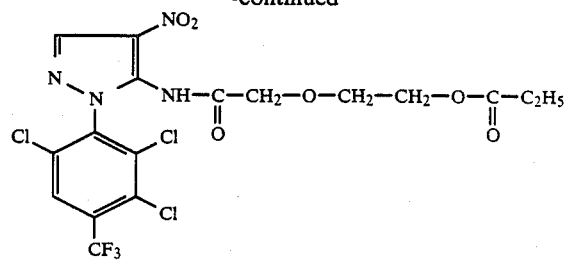

The 5-amino-1-arylpyrazoles necessary as starting substances for carrying out process (a) according to the invention are generally defined by the formula (II). In this formula (II) $R^1$ and Ar preferably represent those radicals which have already been mentioned as preferred for these substituents in connection with the description of the substances of formula (I) according to the invention.

The 5-amino-1-aryl-pyrazoles of the formula (II) are known (cf. U.S. Pat. No. 4,614,533), DE-OS (German Published Specification No. 3,520,330) corresponding to U.S. application Ser. No. 866,638, filed May 22, 1986, now U.S. Pat. No. 4,772,312.

The acylating agents necessary in addition as starting substances for carrying out process (a) according to the invention are generally defined by formula (III). In this formula (III) $A^1$, $A^2$, Y and n preferably represent those radicals and indices which have already been mentioned as preferred for these substituents and indices in connection with the description of the substances of the formula (I) according to the invention. $Hal^1$ preferably represents chlorine or bromine.

The acylating agents of the formula (III) are known

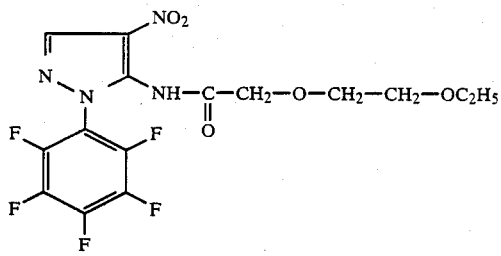

(cf. for example, Nature 160, 149–181 [1947]; DE-OS German Published Specification No. 1,200,279; Liebigs Ann. Chem. 1980, 858–862; U.S. Pat. No. 4,182,711; Neth. Appl. NL No. 65/10,111 of Feb. 6, 1967; French Appl. M FR No. 5509 of Dec. 11, 1967; Neth. NL No. 6,514,035 of May 5, 1966) or can be prepared according to generally conventional methods by analogy with known processes.

The substituted 1-arylpyrazoles necessary as starting substances for carrying out process (b) according to the invention are generally defined by the formula (Ic). In this formula (Ic) $R^1$, $A^1$, $A^2$, Y, Ar and n preferably represent those radicals and indices which have already been mentioned as preferred for these substituents and indices in connection with the description of the substances of the formula (I) according to the invention.

The substituted 1-arylpyrazoles of the formula (Ic) are compounds according to the invention and are obtainable with the aid of process (a), (c) or (d) according to the invention.

The alkylating agents additionally necessary as starting substances for carrying out process (b) according to the invention are generally defined by the formula (IV). In this formula (IV) $R^{2-1}$ preferably represents straight-chain or branched alkyl having 1 to 12, particularly having 1 to 8, carbon atoms.

E preferably represents halogen, in particular chlorine, bromine or iodine or in each case optionally substituted alkylsulphonyloxy, alkoxysulphonyloxy or arylsulphonyloxy such as, for example, methanesulphonyloxy, methoxysulphonyloxy or p-toluenesulphonyloxy.

The alkylating agents of the formula (IV) are generally known compounds of organic chemistry.

The substituted 1-arylpyrazoles necessary as starting substances for carrying out process (c) according to the invention are generally defined by the formula (Ie). In this formula (Ie) $R^2$, $A^1$, $A^2$, Y, Ar and n preferably represent those radicals and indices which have already been mentioned as preferred for these substituents and indices in connection with the description of the substances of the formula (I) according to the invention.

The substituted 1-arylpyrazoles of the formula (Ie) are compounds according to the invention and are obtainable with the aid of process (a), (b) or (d) according to the invention.

The 1-arylpyrazoles necessary as starting substances for carrying out process (d) according to the invention are generally defined by the formula (Ig). In this formula (Ig) $R^1$, $R^2$, $A^1$, $A^2$, Ar and n preferably represent those radicals and indices which have already been mentioned as preferred for these substituents and indices in connection with the description of the substances of the formula (I) according to the invention.

The 1-arylpyrazoles are compounds according to the invention and are obtainable with the aid of process (a), (b) or (c) according to the invention.

The acylating agents further necessary as starting substances for carrying out process (d) according to the invention are generally defined by the formula (VI). In this formula (VI) $R^3$ preferably represents those radicals which have already been mentioned as preferred for these substituents in connection with the description of the substances of the formula (I) according to the invention. $Hal^2$ preferably represents chlorine or bromine. The acylating agents of the formula (VI) are generally known compounds of organic chemistry.

Inert organic solvents are suitable as diluent for carrying out processes (a) and (d) according to the invention.

These include, in particular, aliphatic, alicyclic or aromatic, optionally halogenated hydrocarbons, such as, for example, benzine, benzene, toluene, xylene, chlorobenzene, petroleum ether, hexane, cyclohexane, dichloromethane, chloroform, carbon tetrachloride, ethers, such as diethyl ether, dioxane, tetrahydrofuran or ethylene glycol dimethyl or diethyl ether, ketones such as acetone or butanone, nitriles, such as acetonitrile or propionitrile, amides, such as dimethylformamide, dimethylacetamide, N-methylformanilide, N-methylpyrrolidone or hexamethylphosphoric triamide, esters, such as ethyl acetate, or sulphoxides, such as dimethyl sulphoxide.

Processes (a) and (d) according to the invention can optionally be carried out in the presence of a suitable acid binding agent.

All conventional inorganic or organic bases are suitable as acid binding agents. These include, for example, alkali metal hydroxides, such as sodium hydroxide or potassium hydroxide, alkali metal carbonates, such as sodium carbonate, potassium carbonate or sodium hydrogen carbonate, and also tertiary amines, such as triethylamine, N,N-dimethylaniline, pyridine, N,N-dimethylaminopyridine, diazabicyclooctane (DABCO), diazabicyclononene (DBN) or diazabicycloundecene (DBU).

Processes (a) and (d) according to the invention can optionally be carried out in the presence of a suitable acylation catalyst. As such, use is preferably made of protic acids such as sulphuric acid, hydrochloric acid, phosphoric acid, trifluoroacetic acid or Lewis acids such as aluminum trichloride, boron trifluoride or ferric trichloride.

The reaction temperatures can be varied over a relatively large range in carrying out processes (a) and (d) according to the invention. In general, temperatures between $-20°$ C. and $+150°$ C., preferably temperatures between $0°$ C. and $100°$ C., are used.

For carrying out process (a) according to the invention 1.0 to 15.0 mols, preferably 1.0 to 1.5 mols, of an acylating agent of the formula (III) and optionally 1.0 to 3.0 mols, preferably 1.0 to 2.0 mols, of an acid binding agent and also optionally 0.1 to 3.0 mols, preferably 0.1 to 2.0 mols, of an acylation catalyst are generally employed per mol of 5-amine-1-aryl-pyrazole of the formula (II). The performance of the reaction, work-up and isolation of the reaction products is in accordance with generally customary methods.

For carrying out process (d) according to the invention 1.0 to 15.0 mols, preferably 1.0 to 5.0 mols, of an acylating agent of the formula (VI) and optionally 1.0 to 3.0 mols, preferably 1.0 to 2.0 mols, of an acid binding agent and also optionally 0.1 to 3.0 mols, preferably 0.1 to 2.0 mols, of an acylation catalyst are generally added per mol of 1-arylpyrazole or formula (Ig). The performance of the reaction, work-up and isolation of the reaction products is in accordance with generally customary methods.

Inert organic solvents are likewise suitable as diluents for carrying out process (b) according to the invention. Preferably the organic solvents mentioned in the case of process (a) are used.

Process (b) according to the invention can optionally also be carried out in a two-phase system, such as, for example, water/toluene or water/dichloromethane, optionally in the presence of a phase-transfer catalyst. As examples of such catalysts there may be mentioned: tetrabutylammonium iodide, tetrabutylammonium bromide, tributylmethylphosphonium bromide, trimethyl-$C_{13}/C_{15}$-alkylammonium chloride, dibenzyl-dimethylammonium methylsulphate, dimethyl-$C_{12}/C_{14}$-alkyl-benzylammonium chloride, tetrabutylammonium hydroxide, 15-crown-5, 18-crown-6, triethylbenzylammonium chloride and trimethylbenzylammonium chloride.

All conventionally utilizable inorganic and organic bases are suitable as acid binding agents for carrying out process (b) according to the invention. Alkali metal hydrides, hydroxides, amides, carbonates or hydrogencarbonates, such as, for example, sodium hydride, sodium amide, sodium hydroxide, sodium carbonate or sodium hydrogencarbonate or alternatively tertiary amines, such as, for example, triethylamine, N,N-dimethylaniline, pyridine, 4-(N,N-dimethylamino)-pyridine, diazabicyclooctane (DABCO), diazabicyclononene (DBN) or diazabicycloundecene (DBU), are preferably used.

The reaction temperatures can be varied over a relatively large range in carrying out process (b) according to the invention. In general, temperatures between −20° C. and +150° C., preferably temperatures between 0° C. and +100° C., are used.

For carrying out process (b) according to the invention 1.0 to 20.0 mols, preferably 1.0 to 15.0 mols, of an alkylating agent of the formula (IV) and optionally 1.0 to 3.0 mols, preferably 1.0 to 2.0 mols, of an acid binding agent and also 0.01 to 0.1 mol of a phase-transfer catalyst are generally employed per mol of substituted 1-aryl-pyrazole of the formula (Ic). The performance of the reaction, work-up and isolation of the reaction products of the formula (Ib) takes place in a generally customary form and manner.

All conventional nitrating agents are suitable as nitrating agents for carrying out process (c) according to the invention. Concentrated nitric acid or nitrating acid are preferably used. All solvents conventionally utilizable for such electrophilic substitutions as diluents for carrying out the preparation process (c) are suitable. The acids or mixtures suitable as reagents, such as, for example, nitric acid or nitrating acid, are preferably used simultaneously as diluents. Inert organic solvents such as, for example, glacial acetic acid, or chlorinated hydrocarbons, such as methylene chloride, chloroform or carbon tetrachloride, are also suitable, if desired, as diluents.

The catalysts customary for such reactions are also suitable as catalysts or reaction auxiliaries for carrying out preparation process (c); acid catalysts such as, for example, sulphuric acid, iron-III chloride or other Lewis acids or acetic anhydride are preferably used.

The reaction temperatures can be varied over a relatively large range in carrying out preparation process (c). In general, temperatures between −50° C. and +200° C., preferably between −20° C. and +150° C., are used.

For carrying out preparation process (c), 1.0 to 10.0 mols, preferably 1.0 to 5.0 mols, of a nitrating agent and optionally 0.1 to 10 mols of a catalyst or a reaction auxiliary are generally employed per mol of substituted 1-arylpyrazole of the formula (Ie). The performance of the reaction, work-up and isolation of the reaction products of the formula (Id) takes place in a generally customary form and manner.

The active compounds according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example, on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds according to the invention can be used with particularly good success for selectively combating monocotyledon and dicotyledon weeds, in particular in monocotyledon cultures, such as, for example, wheat or rice.

The active compounds according to the invention engage in the metabolism of the plants and can therefore be employed as growth regulators.

Experience to date of the mode of action of plant growth regulators has shown that an active compound can also exert several different actions on plants. The actions of the compounds depend essentially on the point in time at which they are used, relative to the stage of development of the plant, and on the amounts of active compound applied to the plants or their environment and the way in which the compounds are applied. In every case, growth regulators are intended to influence the crop plants in the particular manner desired.

The amount of leaves on plants can be controlled, under the influence of growth regulators, so that defoliation of the plants at a desired point in time is achieved. Such defoliation is of great importance in the mechanical harvesting of cotton, but is also of interest for facilitating harvesting in other crops, such as, for example, in viticulture. Defoliation of the plants can also be carried out to lower the transpiration of plants before they are transplanted.

Depending on their particular physical and/or chemical properties, the active compounds can be converted to customary formulations, such as solutions, emulsions, suspensions, powders, foams, pastes, granules, aerosoles, natural and synthetic materials impregnated with active compound, very fine capsules in polymeric substances and in coating compositions for seed, furthermore in formulations used with burning equipment, such as fumigating cartridges, fumigating cans, fumigating coils and the like, and also to ULV cold and warm mist formulations.

These formulations are produced in known manner, for example by mixing the active compounds with extenders, that is liquid solvents, liquefied gases under pressure, and/or solid carriers, optionally with the use of surface-active agents, that is emulsifying agents and/or dispersing agents, and/or foam-forming agents. In the case of the use of water as an extender, organic solvents, for example, can also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example, ground natural minerals, such as kaolins, clays, talc, chalk, quartz, attapulgite, montmorillonite or diatomaceous earth, and ground synthetic minerals, such as highly disperse silicic acid, alumina and silicates; as solid carriers for granules there are suitable: for example, crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example, non-ionic and anionic emulsifiers, such as polyoxyethylene-fatty acid esters, polyoxyethylene-fatty alcohol ethers, for example alkylaryl polyglycol ethers, alkylsulphonates, alkyl sulphates, aryl sulphonates as well as albumin hydrolysis products; as dispersing agents there are suitable: for example ligninsulphite waste liquors and methyl-cellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids can be used in the formulations. Further additives may be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

When used as herbicides, the active compounds according to the invention, as such or in the form of their formulations, can also be used, for combating weeds, as mixtures with known herbicides, finished formulations or tank mixes being possible.

Suitable herbicides for the mixtures are known herbicides, such as, for example, 1-amino-6-ethylthio-3-(2,2-dimethylpropyl)-1,3,5-triazine-2,4(1H,3H)-dione or N-(2-benzothiazolyl)-N,N'-dimethylurea for combating weeds in cereals; 4-amino-3-methyl-6-phenyl-1,2,4-triazin-5(4H)-one for combating weeds in sugar beets, and 4-amino-6-(1,1-dimethylethyl)-3-methylthio-1,2,4-triazin-5(4H)-one for combating weeds in soy beans. Mixtures with N,N-dimethyl-N'-(3-chloro-4-methylphenyl)-urea; N,N-dimethyl-N'-(4-isopropylphenyl)-urea; 2-chloro-N-{[(4-methoxy-6-methyl-1,3,5-triazin-2-yl)-amino]-carbonyl}-benzenesulphonamide; 2-{[((4-methoxy-6-methyl-1,3,5-triazin-2-yl)-amino)-carbonyl]-amino-sulphonyl}-benzoic acid or its methyl ester; 4-ethylamino-2-t-butylamino-6-methylthio-s-triazine; 4-amino-6-t-butyl-3-ethylthio-1,2,4-triazin-5(4H)-one; N-methyl-2-(1,3-benzothiazol-2-yloxy)-acetanilide; α-chloro-2',6'-diethyl-N-(2-propoxyethyl)-acetanilide; N,N-diisopropyl-S-(2,3,3-trichloroallyl) thiolcarbamate; N-(1-ethylpropyl)-3,4-dimethyl-2,6-dinitroaniline; methyl 5-(2,4-dichlorophenoxy)-2-nitrobenzoate; methyl 2-[4,5-dihydro-4-methyl-4-(1-methylethyl)-5-oxo-1H-imidazol-2-yl]-4(5)-methylbenzoate; methyl 2-[4-(2,4-dichlorophenoxy)-phenoxy]-propionate; trimethylsilylmethyl 2-[4-(3,5-dichloropyrid-2-yloxy)-phenoxy]-propionate; 3,5-diiodo-4-hydroxybenzonitrile; 3,5-dibromo-4-hydroxybenzonitrile; [(4-amino-3,5-dichloro-6-fluoro-2-pyridyl)oxy]acetic acid or its -1-methylheptyl ester; 2,4-dichlorophenoxy-acetic acid; 2,4-dichlorophenoxypropionic acid; (2-methyl-4-chlorophenoxy)-acetic acid; (4-chloro-2-methylphenoxy)-propionic acid; N-(3,4-dichlorophenyl)-propionamide and 3-isopropyl-2,1,3-benzothiadiazin-4-one 2,2-dioxide are also possible. Surprisingly, some mixtures also exhibit a synergistic action.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, paste and granules. They are used in a customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 10 kg of active compound per hectare of soil surface, preferably between 0.05 and 5.0 kg per ha.

When used as growth regulators, the active compounds according to the invention can also be present in the formulations as a mixture with other known active compounds, such as fungicides, insecticides, acaricides and herbicides, and also as mixtures with fertilizers and other growth regulators.

The active compounds can be used as such, in the form of their formulations or as the use forms prepared therefrom, such as ready-to-use solutions, emulsifiable concentrates, emulsions, foams, suspensions, wettable powders, pastes, soluble powders, dusting agents and granules. They are used in a customary manner, for example by watering, spraying, atomizing, scattering, dusting, foaming, brushing on and the like. It is furthermore possible to apply the active compounds by the ultra-low volume method, or to inject the active compound preparation or the active compound itself into the soil. The seed of the plants can also be treated.

The amounts applied when used as growth regulators can likewise be varied within a substantial range. In general, 0.01 to 50 kg, preferably 0.05 to 10 kg, of active compound are employed per hectare of soil surface.

As regards the time of application, the rule is that the growth regulators are applied within a preferred period of time, the exact definition of which depends on the climatic and vegetative circumstances.

The preparation and the use of the active compounds according to the invention is illustrated by the examples which follow.

Preparation examples

EXAMPLE 1

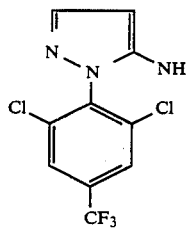

(Process a)

7 ml (0.088 mol) of pyridine and 13.3 g (0.087 mol) of 2-methoxy-ethoxyacetyl chloride (cf. U.S. Pat. No. 4,182,722) are added successively at 20° C. with stirring to 20.5 g (0.069 mol) of 5-amino-1-(2,6-dichloro-4-trifluoromethylphenyl)-pyrazole (cf. DE-OS (German Publication Specification) No. 3,402,308) in 110 ml of acetonitrile, and the mixture is stirred for 12 hours at room temperature. For working-up the mixture is poured into 200 ml of ice water, and the precipitated product is filtered off, washed several times with water and dried in vacuo.

26.6 g (93.3% of theory) of 5-(2-methoxyethoxyacetamido)-1-(2,6-dichloro-4-trifluoromethylphenyl)-pyrazole of melting point 158° C.–160° C. are obtained.

EXAMPLE 2

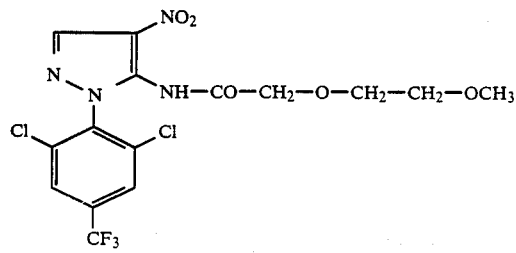

(Process c)

1.4 ml (0.015 mol) of acetic anhydride and 0.5 ml (0.012 mol) of 98 percent strength nitric acid are added successively at about 15° C. to 4.1 g (0.01 mol) of 5-(2-methoxyethoxyacetamido)-1-(2,6-dichloro-4-trifluoromethylphenyl)-pyrazole in 20 ml of glacial acetic acid. After the end of the addition the mixture is stirred for 20 hours at room temperature and poured into 150 ml of ice water, and the precipitated product is filtered off, washed several times with water and dried in vacuo.

4.2 g (92% of theory) of 5-(2-methoxyethoxyacetamido)-4-nitro-1-(2,6-dichloro-4-trifluoromethylphenyl)-pyrazole of melting point 103° C.–105° C. are obtained.

In a corresponding manner and in accordance with the general information on preparation the following substituted 1-arylpyrazoles of the general formula (I) are obtained:

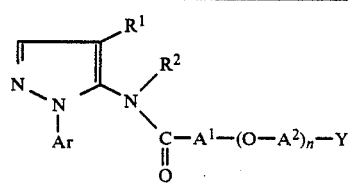

| Ex. No. | $R_1$ | $R_2$ | $A^1-(O-A^2)_n-Y$ | Ar | Physical properties |
|---|---|---|---|---|---|
| 3 | H | H | —CH$_2$—O—(CH$_2$)$_2$—OCH$_3$ | 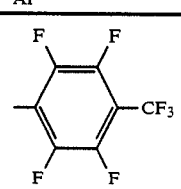 | $^1$H—NMR*: 7,8 |
| 4 | H | H | —CH$_2$—O—CH$_2$—CH$_2$—OCH$_3$ | 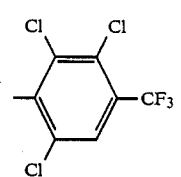 | m.p. 139–142° C. |

-continued
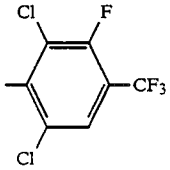
(I)
| Ex. No. | $R_1$ | $R_2$ | $A^1-(O-A^2)_n-Y$ | Ar | Physical properties |
|---|---|---|---|---|---|
| 5 | H | H | $-CH_2-O-CH_2-CH_2-OCH_3$ | 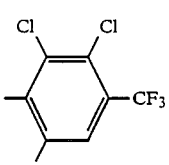 | m.p. 131–133° C. |
| 6 | $NO_2$ | H | $-CH_2-O-CH_2-CH_2-OCH_3$ | 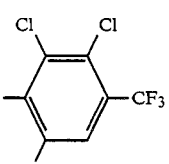 | m.p. 78–86° C. |
| 7 | $NO_2$ | H | $-CH_2-O-CH_2-CH_2-OCH_3$ | 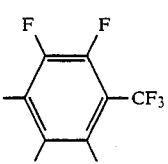 | m.p. 58–61° C. |
| 8 | $NO_2$ | H | $-CH_2-O-CH_2-CH_2-OCH_3$ | 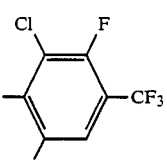 | m.p. 64–66° C. |
| 9 | H | H | $-CH_2-(O-CH_2-CH_2)_2-OCH_3$ | 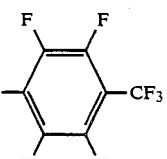 | $^1$H—NMR*: 7.8 |
| 10 | H | H | $-CH_2-(O-CH_2-CH_2)_2-OCH_3$ | 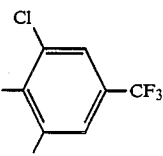 | $^1$H—NMR*: 7.82 |
| 11 | H | H | $-CH_2-(O-CH_2-CH_2)_2-OCH_3$ | 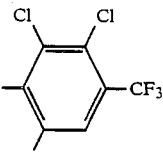 | $^1$H—NMR*: 7.8 |
| 12 | H | H | $-CH_2-(O-CH_2-CH_2)_2-OCH_3$ |  | $^1$H—NMR*: 7.78 |

-continued

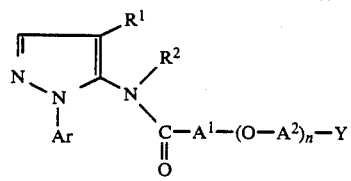
(I)

| Ex. No. | R₁ | R₂ | A¹—(O—A²)ₙ—Y | Ar | Physical properties |
|---|---|---|---|---|---|
| 13 | H | H | —CH₂—(O—CH₂—CH₂)₂—OCH₃ | 2-Cl, 5-CF₃, 4-F phenyl | ¹H—NMR*: 7.78 |
| 14 | NO₂ | H | —CH₂—(O—CH₂—CH₂)₂—OCH₃ | 2,5-Cl₂, 3-F, 4-CF₃ phenyl | m.p. 63–66° C. |
| 15 | NO₂ | H | —CH₂—(O—CH₂—CH₂)₂—OCH₃ | 2,3,5,6-F₄, 4-CF₃ phenyl | m.p. 50–53° C. |
| 16 | NO₂ | H | —CH₂—(O—CH₂—CH₂)₂—OCH₃ | 2,6-Cl₂, 4-CF₃ phenyl | m.p. 44–47° C. |
| 17 | NO₂ | H | —CH₂—(O—CH₂—CH₂)₂—OCH₃ | 2,3,6-Cl₃, 4-CF₃ phenyl | m.p. 62–64° C. |
| 18 | NO₂ | H | —CH₂—(O—CH₂—CH₂)₂—OCH₃ | 2-Cl, 4-CF₃, 6-F phenyl | ¹H—NMR*: 8.38 |
| 19 | NO₂ | H | —CH₂—O—CH₂—CH₂—OCH₃ | 2,3-F₂, 4-CF₃, 6-Cl phenyl | ¹H—NMR*: 8.36 |
| 20 | NO₂ | H | —CH₂—O—CH₂—CH₂—OCH₃ | 2,3-Cl₂, 4-CF₃ phenyl | ¹H—NMR*: 8.36 |

-continued

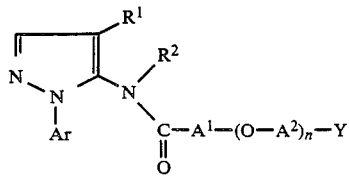
(I)

| Ex. No. | R₁ | R₂ | A¹—(O—A²)ₙ—Y | Ar | Physical properties |
|---|---|---|---|---|---|
| 21 | NO₂ | H | —CH₂—O—CH₂—CH₂—OCH₃ | 3,5-dichloro-4-(CHF₂)phenyl | Oil |
| 22 | NO₂ | H | —CH₂—O—CH₂—CH₂—OCH₃ | 3-Cl, 5-F, 4-CF₃ phenyl | m.p. 88–89° C. |
| 23 | NO₂ | H | —CH₂—O—CH₂—CH₂—OCH₃ | 3-Cl, 2-F, 4-CF₃ phenyl | ¹H—NMR*: 8.34(s) |
| 24 | NO₂ | H | —CH₂—O—CH₂—CH₂—OCH₃ | 3,5-dichloro-4-(SO₂CF₃)phenyl | m.p. 119°–124° C. |
| 25 | NO₂ | H | —CH(CH₃)—O—CH₂—CH₂—OCH₃ | 3,5-dichloro-4-CF₃ phenyl | m.p. 92°–94° C. |
| 26 | NO₂ | H | —CH(CH₃)—O—CH₂—CH₂—OCH₃ | 2,3,5-trichloro-4-CF₃ phenyl | ¹H—NMR° 8.38(s) |
| 27 | NO₂ | H | —CH(CH₃)—O—CH₂—CH₂—OCH₃ | 3-Cl, 2-F, 5-Cl, 4-CF₃ phenyl | ¹H—NMR° 8.39(s) |
| 28 | NO₂ | H | —CH(CH₃)—O—CH₂—CH₂—OCH₃ | 2-F, 5-Cl, 4-CF₃ phenyl | m.p. 77–79° C. |

-continued

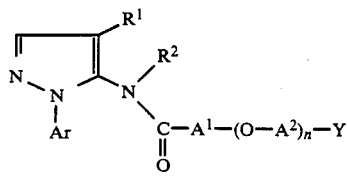
(I)

| Ex. No. | R₁ | R₂ | $A^1-(O-A^2)_n-Y$ | Ar | Physical properties |
|---|---|---|---|---|---|
| 29 | NO₂ | H | $\underset{\underset{\mid}{-CH-O-CH_2-CH_2-OCH_3}}{CH_3}$ | 2,3,5,6-tetrafluoro-4-CF₃-phenyl | ¹H—NMR*: 8.39(s) |
| 30 | NO₂ | H | $\underset{\underset{\mid}{-CH-O-CH_2-CH_2-OCH_3}}{CH_3}$ | 3,5-dichloro-4-SO₂CF₃-phenyl | m.p. 70–79° C. |
| 31 | NO₂ | H | $\underset{\underset{\mid}{-CH-O-CH_2-CH_2-OCH_3}}{CH_3}$ | 2-Cl,4-Cl,3,5-F phenyl | ¹H—NMR* 8.37(s) |
| 32 | NO₂ | H | $\underset{\underset{\mid}{-CH-O-CH_2-CH_2-OCH_3}}{CH_3}$ | 2-Cl,3-F,4-CF₃ phenyl | ¹H—NMR* 8.36(s) |
| 33 | NO₂ | H | $\underset{\underset{\mid}{-CH-O-CH_2-CH_2-OCH_3}}{CH_3}$ | 2,3-dichloro-4-CF₃-phenyl | m.p. 78–86° C. |
| 34 | NO₂ | H | $\underset{\underset{\mid}{-CH-O-CH_2-CH_2-OCH_3}}{CH_3}$ | 2,3-F,4-CF₃,5-Cl phenyl | ¹H—NMR* 8.39(s) |
| 35 | NO₂ | H | $\underset{\underset{\mid}{-CH-O-CH_2-CH_2-OCH_3}}{CH_3}$ | 2-Cl,3-F,4-CF₃,6-F phenyl | ¹H—NMR*: 8.33(s) |

*The ¹-NMR spectra were recorded in CDCl₃ with tetramethylsilane (TMS) as internal standard. The chemical shift of the pyrazole-3-hydrogen is given as δ value in ppm.

Use examples

In the use examples which follow the compound listed below was employed as a comparison substance:

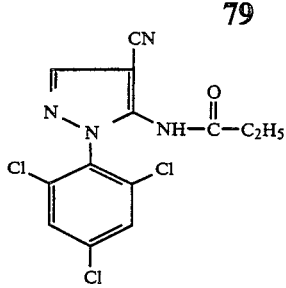

(A)

4-cyano-5-propionamido-1-(2,4,6-trichlorophenyl)-pyrazole (known from DE-OS (German Published Specification) No. 3,226,513)

EXAMPLE A

Pre-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0%=no action (like untreated control)
100%=total destruction

In this test, the compounds according to the preparation Examples 2,6,7 and 8, for example, exhibit distinctly superior activity towards monocotylodon and dicotyledon weeds compared with the comparison substance (A).

EXAMPLE B

Post-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5-15 cm are sprayed with the preparation of active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:

0%=no action (like untreated control)
100%=total destruction

In this test, the compounds according to the preparation Examples 2,6,7 and 8, for example, exhibit distinctly superior efficacy and selectivity for useful plants compared with the comparison substance (A).

EXAMPLE C

Defoliation and desiccation of the leaves of cotton

Solvent: 30 parts by weight of dimethylformamide
Emulsifier: 1 part by weight of polyoxyethylene sorbitan monolaurate To produce a suitable preparation of active compound, 1 part by weight of active compound is mixed with the stated amounts of solvent and emulsifier and the mixture is made up to the desired concentration with water.

Cotton plants are grown in the greenhouse until the 5th secondary leaf has unfolded completely. In this stage, the plants are sprayed with the preparations of active compound until dripping wet. After 1 week, the shedding of leaves and the desiccation of the leaves are rated, in comparison with the control plants.

The figures have the following meanings:

0 denotes no desiccation of the leaves, no shedding of leaves

+ denotes slight desiccation of the leaves, slight shedding of leaves

++ denotes severe desiccation of the leaves, severe shedding of leaves

+++ denotes very severe desiccation of the leaves, very severe shedding of leaves.

The compounds according to the preparation Examples 2,6,7 and 8, for example, exhibit a very good activity.

It will be appreciated that the instant specification and claims are set forth by way of illustration and not limitation, and that various modifications and changes may be made without departing from the spirit and scope of the present invention.

What is claimed is:

1. A substituted 1-arylpyrazole of the formula

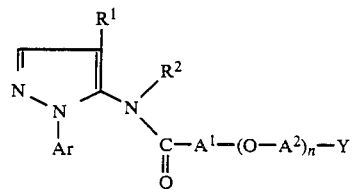

in which
R$^1$ represents hydrogen or nitro,
R$_2$ represents hydrogen, straight-chain or branched alkyl having 1 to 12 carbon atoms or a radical,

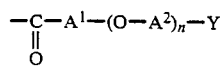

A$^1$ and A$^2$, independently of one another, in each case represent an in each case straight-chain or branched divalent alkylene radical having 1 to 6 carbon atoms, Y represents halogen, hydroxyl, straight-chain or branched alkoxy having 1 to 6 carbon atoms which is optionally monosubstituted or polysubstituted by halogen, cyano or nitro, the substituents being identical or different, or optionally monosubstituted or polysubstituted phenyloxy, the substituents being identical or different and selected from the group consisting of halogen, cyano, nitro, in each case straight-chain or branched alkyl, alkoxy, alkylthio, halogenoalkyl, halogenoalkoxy, halogenoalkylthio or alkoxycarbonyl in each case having 1 to 4 carbon atoms and, if appropriate, 1 to 9 identical or different halogen atoms, or represents a

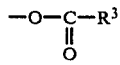

radical, where

R³ represents hydrogen, amino, in each case straight-chain or branched alkyl, alkoxy, alkylamino or dialkylamino in each case having 1 to 6 carbon atoms in the individual alkyl parts, or in each case optionally monosubstituted or polysubstituted phenyl, phenoxy or phenylamino, the substituents being identical or different and selected from the group consisting of halogen, cyano, nitro, in each case straight-chain or branched alkyl, alkoxy, alkylthio, halogenoalkyl, halogenoalkoxy, halogenoalkylthio or alkoxycarbonyl in each case having 1 to 4 carbon atoms, and, if appropriate, 1 to 9 identical or different halogen atoms, represents in each case optionally monosubstituted or polysubstituted phenyl, 2-pyridyl, 3-pyridyl or 4-pyridyl, the substituents being identical or different and selected from the group consisting of halogen, cyano, nitro, in each case straight-chain or branched alkyl, alkoxy or alkoxycarbonyl, in each case having 1 to 4 carbon atoms in the alkyl parts, in each case straight-chain or branched halogenoalkyl or halogenalkoxy in each case having 1 to 4 carbon atoms and 1 to 9 identical or different halogen atoms, or a —S(O)$_m$—R⁴ radical where R⁴ represents amino, in each case straight-chain or branched alkyl, alkylamino, dialkylamino or halogenoalkyl, in each case having 1 to 4 carbon atoms in the individual alkyl parts and, in the case of halogenoalkyl having 1 to 9 identical or different halogen atoms, and m represents a number 0, 1 or 2, and
n represents a number 1, 2, 3, or 4.

2. A compound according to claim 1, in which
R² represents hydrogen, straight-chain or branched alkyl having 1 to 8 carbon atoms or a

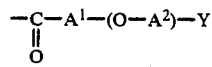

radical,
A¹ and A², independently of one another, in each case represent an in each case straight-chain or branched divalent alkylene radical having 1 to 4 carbon atoms,
Y represents fluorine, chlorine, bromine, iodine, hydroxyl, straight-chain or branched alkoxy having 1 to 4 carbon atoms, or optionally monosubstituted, disubstituted or trisubstituted phenyloxy, the substituents being identical or different and selected from the group consisting of fluorine, chlorine, bromine, cyano, nitro, methyl, ethyl, n- or i-propyl, n-, i-, s- or t-butyl, methoxy, ethoxy, methylthio, trifluoromethyl, trifluoromethoxy, trifluoromethylthio, methoxycarbonyl or ethoxycarbonyl; or represents a

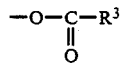

radical,
R³ represents hydrogen, amino, in each case straight-chain or branched alkyl, alkoxy, alkylamino or dialkylamino in each case having 1 to 4 carbon atoms in the individual alkyl parts, or in each case optionally monosubstituted, disubstituted or trisubstituted phenyl, phenoxy or phenylamino, the substituents being identical or different and selected from the group consisting of fluorine, chlorine, bromine, cyano, nitro, methyl, ethyl, n- or i-propyl, n-, i-, s- or t-butyl, methoxy, ethoxy, methylthio, trifluoromethyl, trifluoromethoxy, trifluoromethylthio, methoxycarbonyl or ethoxycarbonyl,
Ar represents optionally monosubstituted to pentasubstituted phenyl, the substituents being identical or different and suitable substituents being cyano, nitro, fluorine, chlorine, bromine, iodine, methyl, ethyl, n- or i-propyl, n-, i-, s- or t-butyl, methoxy, ethoxy, methoxycarbonyl, ethoxycarbonyl, trifluoromethyl, trichloromethyl, dichlorofluoromethyl, difluorochloromethyl, chloromethyl, dichloromethyl, difluoromethyl, pentafluoroethyl, tetrafluoroethyl, trifluorochloroethyl, trifluoroethyl, difluorodichloroethyl, trifluorodichloroethyl, pentachloroethyl, trifluoromethoxy, trichloromethoxy, dichlorofluoromethoxy, difluorochloromethoxy, chloromethoxy, dichloromethoxy, difluoromethoxy, pentafluoroethoxy, tetrafluoroethoxy, trifluorochloroethoxy, trifluoroethoxy, difluorodichloroethoxy, trifluorodichloroethoxy, pentachloroethoxy or an —S(O)$_m$—R⁴ radical, or represents 2-pyridyl, 3-pyridyl or 4-pyridyl which is in each case optionally monosubstituted to tetrasubstituted by the same substituents as for phenyl, the substituents being identical or different, where R⁴ represents amino, methylamino, ethylamino, dimethylamino, diethylamino, fluorodichloromethyl, difluoromethyl, tetrafluoroethyl, trichloroethyl, trifluoromethyl, difluorochloromethyl, methyl or ethyl, and
m represents a number 0, 1 or 2.

3. A compound according to claim 1, in which
R¹ represents nitro,
R² represents hydrogen, methyl, ethyl, n- or i-propyl, n-, i-, s- or t-butyl or a

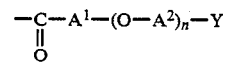

radical,
A¹ and A², independently of one another, in each case represent a bridging group of the formula —CH₂—; —CH₂—CH₂;

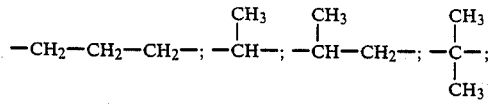

-continued

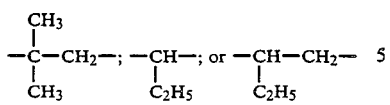

Y represents fluorine, chlorine, bromine, methoxy, ethoxy, n- or i-propoxy, n- or i-butoxy or hydroxyl, Ar represents optionally monosubstituted to pentasubstituted phenyl, the substituents being identical or different and selected from the group consisting of cyano, nitro, fluorine, chlorine, bromine, iodine, methyl, ethyl, n- or i-propyl, n-, i-, s- or t-butyl, methoxy, ethoxy, methoxycarbonyl, ethoxycarbonyl, trifluoromethyl, trichloromethyl, dichlorofluoromethyl, difluorochloromethyl, chloromethyl, dichloromethyl, difluoromethyl, pentafluoroethyl, tetrafluoroethyl, trifluorochloroethyl, trifluoroethyl, difluorodichloroethyl, trifluorodichloroethyl, pentachloroethyl, trifluoromethoxy, trichloromethoxy, dichlorofluoromethoxy, difluorochloromethoxy, chloromethoxy, dichloromethoxy, difluoromethoxy, pentafluoroethoxy, tetrafluoroethoxy, trifluorochloroethoxy, trifluorethoxy, difluorodichloroethoxy, trifluorodichloroethoxy, pentachloroethoxy or an —S(O)$_m$—R$^4$ radical, or represents 2-pyridyl which is optionally monosubstituted to tetrasubstituted by the same substituents as for phenyl, the substituents being identical or different, where R$^4$ represents amino, methylamino, ethylamino, dimethylamino, diethylamino, fluorodichloromethyl, difluoromethyl, tetrafluoroethyl, trichloroethyl, trifluoromethyl, difluorochloromethyl, methyl or ethyl, m represents a number 0, 1 or 2 and n represents a number 1 or 2.

4. A compound according to claim 1, wherein such compound is 5-(2-methoxyethoxyacetamido)-4-nitro-1-(2,6-dichloro-4-trifluoromethylphenyl)-pyrazole of the formula

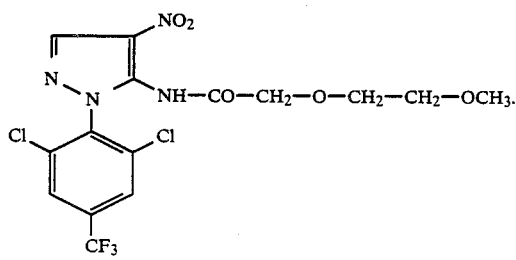

5. A compound according to claim 1, wherein such compound is 5-(2-methoxyethoxyacetamido)-4-nitro-1-(2,6-dichloro-3-fluoro-4-trifluoromethylphenyl)-pyrazole of the formula

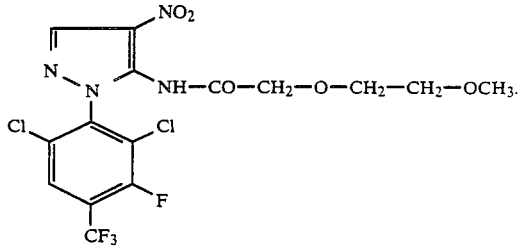

6. A compound according to claim 1, wherein such compound is 5-(2-methoxyethoxyacetamido)-4-nitro-1-(2,3,5,6-tetrafluoro-4-trifluoromethylphenyl)-pyrazole of the formula

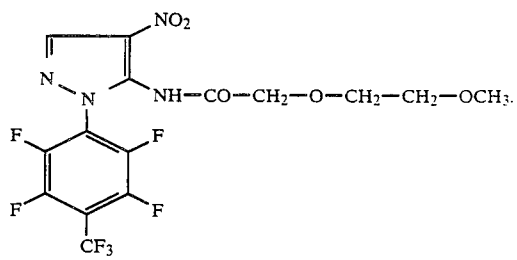

7. A compound according to claim 1, wherein such compound is 5-(2-methoxyethoxyacetamido)-4-nitro-1-(6-chloro-2,3-difluoro-4-trifluoromethylphenyl)-pyrazole of the formula

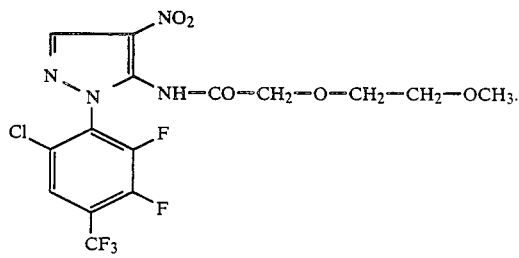

8. A herbicidal and plant growth regulating composition comprising an amount effective therefor of a compound according to claim 2 and a diluent.

9. A method of regulating the growth of plants which comprises applying to such plants or to a locus in which such plants are growing or are to be grown a plant growth-regulating effective amount of a compound according to claim 2.

10. The method according to claim 9, wherein such compound is 5-(2-methoxyethoxyacetamido)-4-nitro-1-(2,6-dichloro-4-trifluoromethylphenyl)pyrazole, 5-(2-methoxyethoxyacetamido)-4-nitro-1-(2,6-dichloro-3-fluoro-4-trifluoromethylphenyl)pyrazole, 5-(2-methoxyethoxyacetamido)-4-nitro-1-(2,3,5,6-tetrafluoro-4-trifluoromethylphenyl)pyrazole, or 5-(2-methoxyethoxyacetamido)-4-nitro-1-(6-chloro-2,3-difluoro-4-trifluoromethylphenyl)pyrazole.

11. A method of killing unwanted vegetation which comprises applying to such vegetation or to a locus from which it is desired to exclude such vegetation a herbicidally effective amount of a compound according to claim 1.

12. The method according to claim 11, wherein such compound is 5-(2-methoxyethoxyacetamido)-4-nitro-1-(2,6-dichloro-4-trifluoromethylphenyl)pyrazole, 5-(2-methoxyethoxyacetamido)-4-nitro-1-(2,6-dichloro-3-fluoro-4-trifluoromethylphenyl)pyrazole, 5-(2-methoxyethoxyacetamido)-4-nitro-1-(2,3,5,6-tetrafluoro-4-trifluoromethylphenyl)pyrazole, or 5-(2-methoxyethoxyacetamido)-4-nitro-1-(6-chloro-2,3-difluoro-4-trifluoromethylphenyl)pyrazole.

* * * * *